(12) United States Patent
Gumennik et al.

(10) Patent No.: US 10,338,000 B2
(45) Date of Patent: Jul. 2, 2019

(54) FIBER SENSOR

(71) Applicants: Massachusetts Institute of Technology, Cambridge, MA (US); FLIR Systems, Incorporated, Wilsonville, OR (US)

(72) Inventors: Alexander Gumennik, Brookline, MA (US); Alexander Mark Stolyarov, Belmont, MA (US); Brent Richard Schell, Stoughton, MA (US); Chong Hou, Cambridge, MA (US); Guillaume Romain Lestoquoy, Cambridge, MA (US); Fabien Sorin, Saintj-Sulpice (FR); William Richard McDaniel, II, Worcester, MA (US); Yoel Fink, Brookline, MA (US); Aimee Rose, Cambridge, MA (US); John Dimitris Joannopoulos, Belmont, MA (US)

(73) Assignees: Massachusetts Institute of Technology, Cambridge, MA (US); FLIR Systems, Incorporated, Wilsonville, OR (US)

( * ) Notice: Subject to any disclaimer, the term of this patent is extended or adjusted under 35 U.S.C. 154(b) by 750 days.

(21) Appl. No.: 14/035,933

(22) Filed: Sep. 24, 2013

(65) Prior Publication Data
US 2014/0212084 A1 Jul. 31, 2014

Related U.S. Application Data

(60) Provisional application No. 61/704,857, filed on Sep. 24, 2012.

(51) Int. Cl.
*G01N 21/77* (2006.01)
*G01N 21/76* (2006.01)
(Continued)

(52) U.S. Cl.
CPC ....... *G01N 21/84* (2013.01); *B29D 11/00721* (2013.01); *G01N 21/76* (2013.01);
(Continued)

(58) Field of Classification Search
None
See application file for complete search history.

(56) References Cited

U.S. PATENT DOCUMENTS 4,824,789 A * 4/1989 Yafuso ............... A61B 5/1459
250/227.23
6,579,722 B1 * 6/2003 Collins ............... G01N 21/766
356/39
(Continued)

FOREIGN PATENT DOCUMENTS

JP 06-273227 A 9/1994

OTHER PUBLICATIONS

PCT/US2013/061503, International Search Report, Form PCT/ISA/210 first sheet, second sheet, and patent family annex, dated Jan. 2014.
(Continued)

*Primary Examiner* — Neil N Turk
(74) *Attorney, Agent, or Firm* — Theresa A. Lober

(57) ABSTRACT

There is provided a sensor fiber including an electrically insulating material having a fiber length. At least one transduction element is disposed along at least a portion of the fiber length and is arranged for exposure to an intake species. A photoconducting element is in optical communication with the transduction element. At least one pair of electrically conducting electrodes are in electrical connection with the photoconducting element. The pair of electrodes extend the fiber length.

34 Claims, 7 Drawing Sheets

(51) Int. Cl.
*G01N 21/84* (2006.01)
*G02B 6/42* (2006.01)
B29D 11/00 (2006.01)
*G02B 6/02* (2006.01)

(52) U.S. Cl.
CPC ....... *G01N 21/7703* (2013.01); *G02B 6/4283* (2013.01); *C03B 2201/86* (2013.01); *G01N 2021/7753* (2013.01); *G01N 2021/7786* (2013.01); *G02B 6/02314* (2013.01); *G02B 6/4291* (2013.01)

(56) References Cited

U.S. PATENT DOCUMENTS

| | | | |
|---|---|---|---|
| 7,041,910 B2 | 5/2006 | Swager et al. | |
| 7,054,513 B2 * | 5/2006 | Herz | B82Y 20/00 385/12 |
| 7,208,122 B2 | 4/2007 | Swager et al. | |
| 7,292,758 B2 | 11/2007 | Bayindir et al. | |
| 7,462,325 B2 | 12/2008 | Hancock | |
| 7,759,127 B2 | 7/2010 | Rose et al. | |
| 7,799,573 B2 * | 9/2010 | Deans | C07D 471/14 422/52 |
| 7,964,022 B2 | 6/2011 | Harvey | |
| 2003/0178607 A1 | 9/2003 | Swager et al. | |
| 2005/0053345 A1 * | 3/2005 | Bayindir | B29D 11/00663 385/123 |
| 2007/0019917 A1 | 1/2007 | Bayindir et al. | |
| 2007/0065075 A1 | 3/2007 | Berger et al. | |
| 2008/0204758 A1 | 8/2008 | Yates et al. | |
| 2008/0272311 A1 | 11/2008 | Egalon | |

OTHER PUBLICATIONS

PCT/US2013/061503, Written Opinion of the International Searching Authority, Form PCT/ISA/237 cover sheet, Box No. 1 sheet, Box No. V sheet, and Supplemental Box sheet, dated Jan. 2014.
Gumennik et al., "All-in-Fiber Chemical Sensing," Advanced Materials, vol. 24, pp. 6005-6009, Oct. 2012.
Stolyarov et al., "Enhanced chemiluminescent detection scheme for trace vapor sensing in pneumatically-tuned hollow core photonic bandgap fibers," Optics Express, vol. 20, No. 11, pp. 12407-12415, May 2012.
Stolyarov et al., "Fabrication and characterization of fibers with built-in liquid crystal channels and electrodes for transverse incident-light modulation," Applied Physics Letters, vol. 101, pp. 011108-1-01108-4, Jul. 2012.
Tao et al., "Multimaterial Fibers," Int. Jnl. of Applied Glass Science, vol. 3, No. 4, pp. 349-368, Nov. 2012.

* cited by examiner

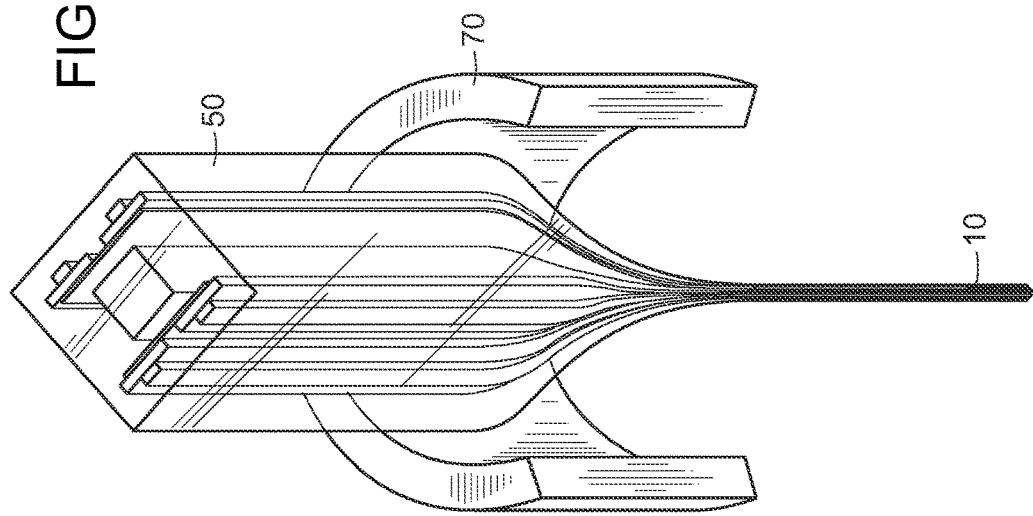
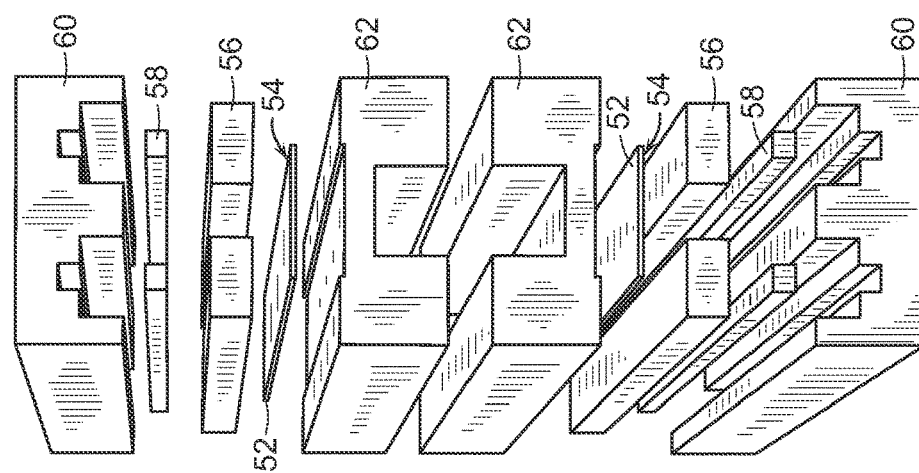

FIBER SENSOR

CROSS-REFERENCE TO RELATED APPLICATIONS

This application claims the benefit of U.S. Provisional Application No. 61/704,857, filed Sep. 24, 2012, the entirety of which is hereby incorporated by reference.

STATEMENT REGARDING FEDERALLY SPONSORED RESEARCH

This invention was made with Government support under Contract No. DMR-0819762, awarded by the National Science Foundation, and under Contract No. W911NF-07-D-0004, awarded by the United States Army Research Office. The Government has certain rights in the invention.

BACKGROUND

This invention relates generally to sensing, and more particularly relates to optical fiber-based sensing.

Optical fibers can be employed for sensing in a wide range of applications, and are particularly advantageous for remote chemical sensing applications. In a remote chemical sensing arrangement, an optical fiber can be configured to collect an emissive signal at one fiber end and transmit such signal to a detector that is positioned remotely at an opposite fiber end. The emissive signal can in general be, e.g., a luminescent signal, such as a chemiluminescent (CL) signal, and can be transmitted optically by the optical fiber from a sensing location to a remote detection location. This remote optical fiber sensing configuration can be of particular interest for detection of hazardous materials, such as explosives.

Inherent to a remote optical fiber sensing arrangement are several significant limitations. First, the achievable remoteness of the detection function from the sensing location, as well as the detection sensitivity, are restricted by the numerical aperture (NA) of the optical fiber, the optical fiber transmission and bending losses, and the sensitivity of the detector. While the NA can be increased with particular fiber configurations, such as a hollow core photonic bandgap (PBG) fiber configuration, and highly sensitive photodetectors can be implemented, limitations on coupling efficiency and propagation losses present challenges to distributed optical fiber sensing over large areas.

SUMMARY

There is provided a sensor fiber including an electrically insulating material having a fiber length. At least one transduction element is disposed along at least a portion of the fiber length and is arranged for exposure to an intake species. A photoconducting element is in optical communication with the transduction element. At least one pair of electrically conducting electrodes are in electrical connection with the photoconducting element. The pair of electrodes extend the fiber length.

With this configuration, the sensor fiber can internally convert a transduction signal into an electrical signal at the site of detection in the fiber and transmit the electrical signal to a fiber end, which can be significantly remote from the site of detection. As a result, the sensor fiber provides the benefits of both sensor signal production at the site of detection and distributed and remote sensing capabilities. This sensor fiber configuration can be applied to any sensing environment for a selected species detection. Chemical detection, particle detection, acoustic detection, electromagnetic detection, e.g., of varying wavelengths, radioactive detection, and other species detection can be conducted. The sensor fiber thereby provides all of electrical, optical, and transduction functionality that can be tailored for sensing a selected species. This approach maximizes electrical sensing signal collection efficiency and eliminates the performance disadvantages associated with optical sensing signal transmission.

Other features and advantages of the sensor fiber will be apparent from the following description and accompanying drawings, and from the claims.

BRIEF DESCRIPTION OF THE DRAWINGS

FIG. 4 is a schematic exploded perspective view of a preform that was employed for producing an example sensor fiber;

FIG. 5 is a schematic view depicting the fiber drawing process for producing a sensor fiber from the preform of FIG. 4;

DETAILED DESCRIPTION

Figure 1A:
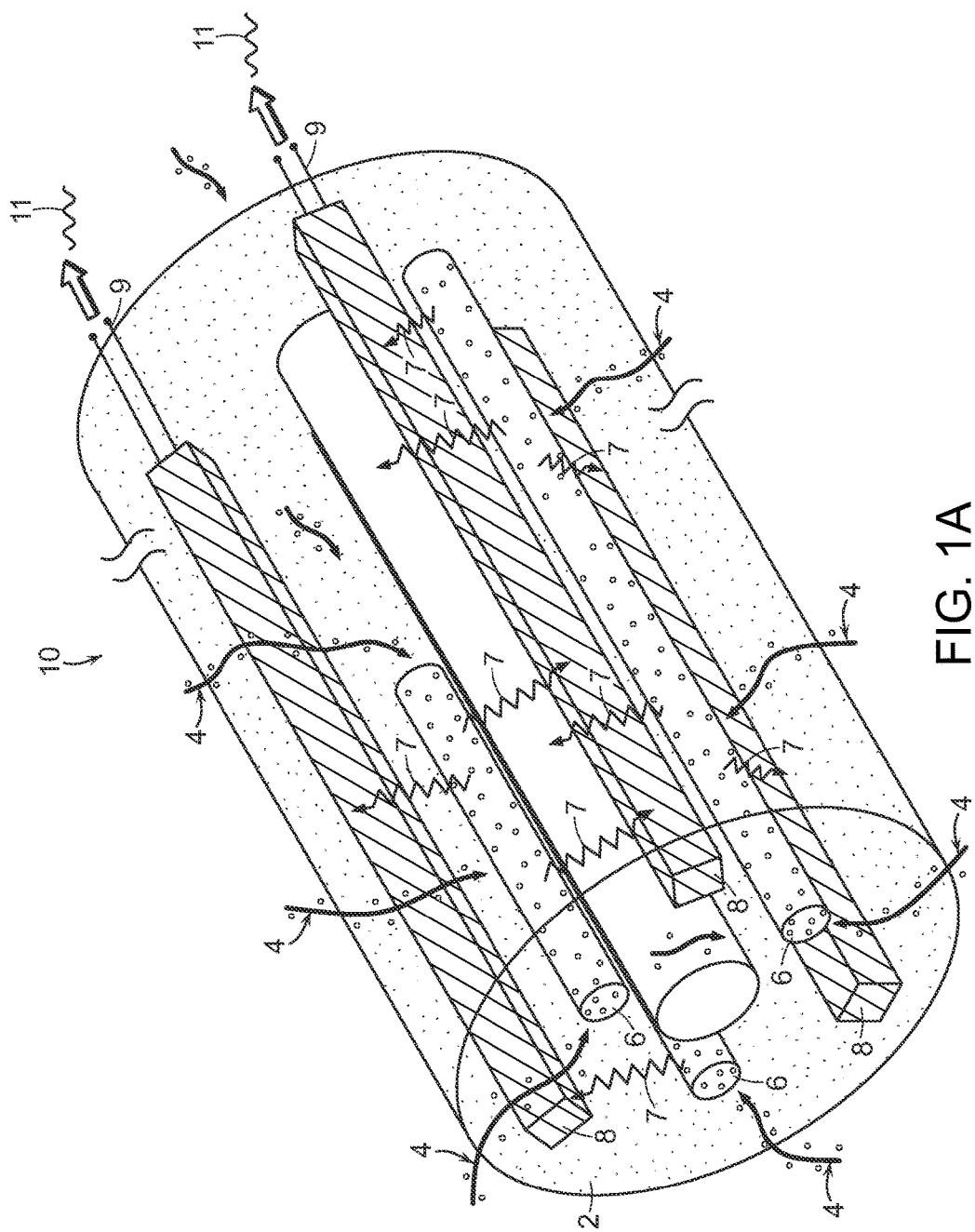
FIG. 1A is a schematic perspective view of a sensor fiber including a transduction element, a photodetecting element, and electrical signal transmission elements for delivering from the sensor fiber an electrical sensing signal.

FIG. 1A is a schematic perspective view of an example sensor fiber 10. The sensor fiber monolithically integrates into a single fiber all elements for enabling complete sensor functionality, including intake of a species to be sensed, interaction or reaction of the species to be sensed with a transduction element, photodetection of the species to be sensed, and production of an electrical signal indicative of the sensing, delivered at the end of the sensor fiber. Examples of the sensor fiber elements for these functionalities are shown schematically in FIG. 1A. The sensor fiber 10 has a fiber length that can be a conventional optical fiber length, e.g., tens or hundreds of meters. The sensor fiber body 2 is provided along the fiber length with a suitable material such as an electrically insulating material. Species 4 in the vicinity of the fiber can enter into and/or through the fiber body 2 to reach one or more transduction elements 6. As the species 6 taken into the fiber interacts with the transduction elements 6, the transduction elements transfer the energy of that species interaction into an optical signal 7. The optical signal 7 travels through the fiber and is detected by at least one photodetector 8. Each photodetector includes electrical transmission elements 9 that transmit a photodetection signal 11 out of the sensor fiber 10.

With this configuration, the sensor fiber internally converts a transduction signal into an electrical signal at the site of detection in the fiber and transmits the electrical signal to the fiber end, which can be significantly remote from the site of detection. As a result, the sensor fiber provides the benefits of both sensor signal production at the site of detection and distributed and remote sensing capabilities. This sensor fiber configuration can be applied to any sensing environment for a selected species detection. Chemical detection, particle detection, acoustic detection, electromagnetic detection, e.g., of varying wavelengths, radioactive detection, and other species detection can be conducted. To achieve detection for a given species of interest, there is provided within the sensor fiber a corresponding transduction element that can interact with the species of interest and convert energy that is associated with that interaction into a corresponding level of an optical signal. The optical signal can be increased or decreased from a quiescent level, which can be zero; in any of these scenarios, the optical signal is produced in the sensor fiber for detection of the selected species by a photodetector in the fiber. Any suitable transduction element that enables such optical sensing can therefore be employed. The sensor fiber thereby provides all of electrical, optical, and transduction functionality that can be tailored for sensing a selected species.

Figure 1B:
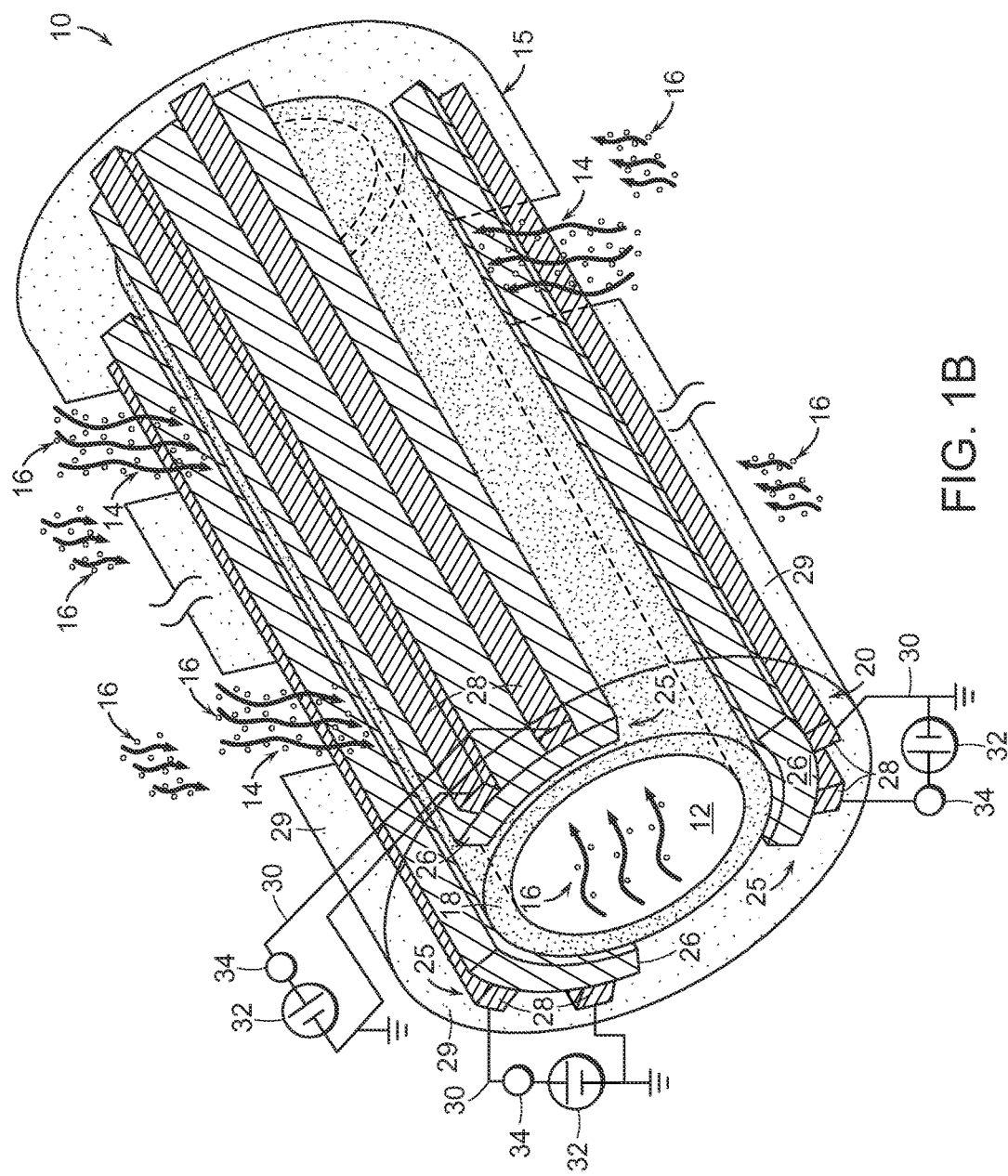
FIG. 1B is an example sensor fiber embodiment including a species intake conduit, a species sensing material, photodetectors, and electrical signal transmission elements all provided within the sensor fiber.

In one example embodiment of the sensor fiber, shown schematically in FIG. 1B, intake and delivery of a species to be sensed is tailored for delivery of a liquid, gas, or other suitable medium into the fiber to the transduction element. In this example, within the fiber, there is included at least one hollow conduit, or microcapillary 12, that extends the full length of the fiber. In addition, there further can be included one or more intake apertures 14 in the fiber wall 15 at selected sites along the length of the fiber. With the one or more hollow microcapillaries 12 and intake apertures 14 provided in the fiber, the fiber can accept a species 16 that is present in the local environment of the fiber. The species can take any form, and be provided in any suitable carrier medium, including, e.g., liquid phase or gaseous phase media.

The sensor fiber 10 includes one or more transduction elements that in this example include sensing materials, such as a chemiluminescent material that emits light upon reaction with a corresponding intake species. In the example configuration of FIG. 1B, one or more hollow microcapillaries 12 each host a transduction element sensing material 18 that is here provided as a layer of luminescent or chemiluminescent material. The transduction element sensing material 18 extends for at least a portion of the fiber 10, and can be disposed at one end of the fiber. For many applications, the transduction element sensing material can preferably extend the entire length of the fiber 10. A surface of the sensing material 18 is in fluidic communication with the microcapillary 12, so that the sensing material 18 can interact with, and for selected materials, react, with a species 12 that is taken into the hollow microcapillary at an end 20 of the fiber, or taken into the microcapillary by way of intake apertures along the fiber length. The term "fluidic communication" is therefore meant herein to refer to the ability of a vapor or liquid to be accessible from the microcapillary to the sensing material.

During interaction or reaction of a sensing material 18 with a species taken into the fiber microcapillary 12, the sensing material produces light, e.g., luminescence, due to the interaction or reaction, with the light having a wavelength that is indicative of the intake species. Alternatively, the sensing material can produce quiescent illumination that is altered by interaction with an intake species, e.g., to increase, decrease, or quench the quiescent illumination. The illumination from the sensing material is detected by one or more photodetectors 25 that are integrated into the fiber 10 along at least a portion of the fiber length and that can each extend along the entire fiber length. Each photodetector includes a photoconducting material element 26 that is electrically connected to at least one, and preferably two, electrically conductive electrodes 28. Both the photoconducting material element 26 and the electrodes 28 extend along at least a portion of the fiber length and all can extend along the entire fiber length. A fiber cladding material 29 is provided around the elements of the fiber 10, e.g., as a protective outer coating, and preferably is an electrically insulating material that electrically isolates each photodetector in the fiber.

Figure 2:
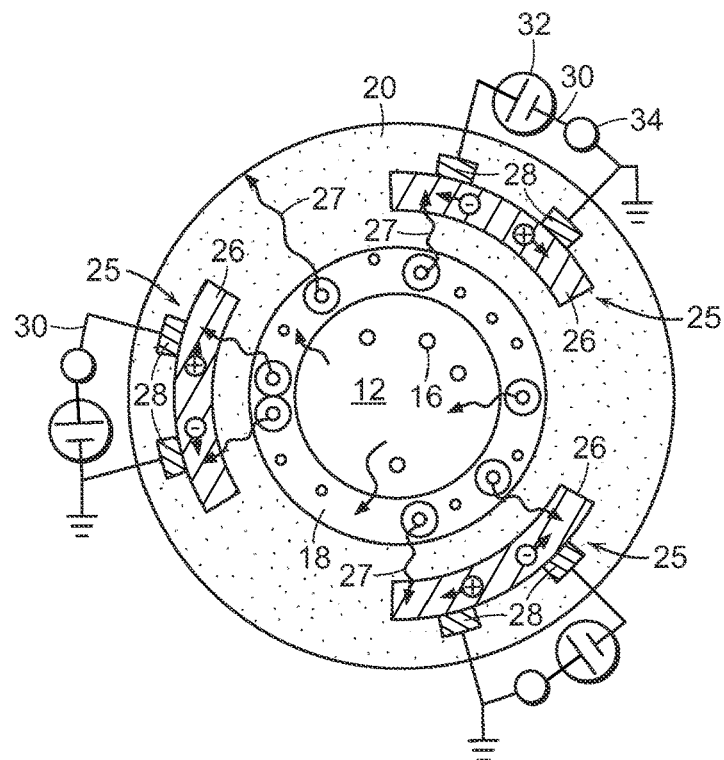
FIG. 2 is a schematic end view of the example sensor fiber of FIG. 1B, illustrating emission from a species sensing material for detection by in-fiber photodetectors.

Referring also to the schematic representation of FIG. 2, and as shown in FIG. 1B, each photodetector 25 is connected in a corresponding sensing circuit 30 that can be arranged in a suitable manner, e.g., external to the fiber 10. For connection to an external circuit, a pair of electrodes 28 can extend the length of the fiber 10 and be connected in the circuit. The circuit applies a bias voltage between the electrodes, for electrically biasing the photoconducting material. As the intake species 16 enters the microcapillary 12, the species 16 comes into the vicinity of the sensing element 18 and can interact or react with the element 18. Such reaction or interaction can produce light 27 that is emitted from the sensing material. This illumination reaches the photoconducting material 26 and causes the generation of photo-induced electron-hole pairs at the surface of the photoconducting material. Once such electrical charges are generated, the charges are separated by the electric field that is produced between the electrodes by the bias voltage, with holes and electrons swept towards opposing electrodes. The charge carriers then are conducted by the electrodes through the fiber and out of the fiber to the connected circuit. The electrodes thereby provide transmission of an electrical sensing signal to the sensing circuit directly from the transduction site of a transduction element sensing material and a corresponding photodetector.

With this operation, within the sensor fiber itself there is produced the electrical sensing signal, at the site of photodetectors in the fiber, along the fiber length. As a result, an electrical sensing signal, rather than optical sensing signal, is transmitted from the fiber directly to a sensing circuit. No optical transmission is required to capture a sensing signal from the fiber. Instead, the fiber directly electrically connects to sensing circuitry for sensing signal readout. This approach maximizes electrical sensing signal collection efficiency and eliminates the performance disadvantages associated with optical sensing signal transmission.

As shown in FIGS. 1-2, each sensing circuit 30 includes, e.g., a voltage source 32 and ammeter or current amplifier 34, or other suitable circuit elements, for applying a voltage across a photoconducting material element 26 in the fiber and for measuring current flow through the photoconducting material element 26, respectively. No particular voltage polarity is required, and any suitable voltage generation means can be employed. With this configuration, there is indicated by an electronic circuit signal, such as an electrical current level, the detection of a species that has been taken into a fiber and that has interacted or reacted with a transduction element, such as the sensing material 18, to produce a change in electrical current flow through a photoconducting material element, e.g., in correspondence with the composition or concentration of the intake species.

As demonstrated by this example embodiment, the sensor fiber provides a monolithically-integrated sensor that accomplishes all of the functions of species intake, species delivery for interaction with a transduction element, detection of transduced energy due to species interaction, and corresponding electronic detection signal production. These functions are integral to the fiber along the fiber length. The small footprint, potential for multiplexing, flexible form factor, scalable manufacturing, and compatibility with miniaturized electronics of the sensor fiber 10 enable remote and distributed sensing configurations that provide superior performance for a wide range of sensing applications.

The sensor fiber 10 is a three-dimensional, unsupported solid state object for which one dimension, defined as the longitudinal dimension, defining the fiber length, is substantially larger than the other two dimensions, defined as the cross sectional dimensions of the fiber. The fiber is produced by, e.g., a thermal fiber drawing process like that employed for producing optical fibers, as described in detail below. Briefly, first a macroscopic fiber preform is assembled and then thermally consolidated, and the consolidated preform is then thermally drawn to form a sensor fiber that includes elements which were arranged in the fiber preform. The fiber preform can include materials that are electrically conducting, semiconducting, and insulating, and those materials are assembled into the fiber preform to provide one or more of the sensing functionalities just described. The preform includes selected materials arranged in a macroscopic geometric configuration corresponding to, though not necessarily equivalent to, the desired geometry of the sensor fiber. The preform is characterized by a ratio of longitudinal to cross sectional dimensions that is typically between about 2 and about 100. Once assembled, the preform can be consolidated under selected temperature and pressure conditions as described below, to produce intimate material interfaces in the preform and to ensure element shape integrity throughout the draw process. The preform is then drawn into a sensor fiber that reduces preform feature sizes to smaller scales, on the microscale, and produces extended fiber lengths of uniform cross section.

The striking dimensional shift enabled by the fiber drawing process thereby produces a microscopic sensor fiber arrangement of fiber elements from the macroscopic arrangement of preform elements. Consider a macroscopic assembly of conducting, semiconducting, and insulating materials arranged as a sensor fiber preform having a diameter, D on the order of about 10 mm to about 100 mm and a length, L, on the order of centimeters, e.g., less than about 100 cm. The structured preform is then subjected to heating and deformation under fiber drawing conditions to produce a sensor fiber having a length, l, on the order of meters, e.g., 10 m, 20 m, 50 m, 100 m, or longer, and a diameter, d, on the order of between about 50 µm and about 2000 µm, resulting in a longitudinal-to-cross sectional ratio that can be above 1000, a length that can be more than 100 times greater than that of the preform, and a diameter that can be 10 times less than the diameter of the preform. Within the sensor fiber, feature sizes of the transduction element and photodetectors on the order of 10's of nanometers can be produced. The sensor fiber drawing process preserves element organization along the length of the sensor fiber while forming intimate material interfaces and reducing element sizes to the micro- and nano-scale along the sensor fiber length. As a result, there can be produced a microscopic, extended-length sensor fiber including inlet ports, such as species intake microcapillaries, transduction elements, such as sensing materials, photodetectors, and electrical signal transmission elements without employing wafer-based microfabrication techniques.

Turning to particulars of the sensor fiber elements, the fiber can be configured in any suitable manner to accommodate intake of a species to be detected. For many species, such as electromagnetic radiation or optical illumination, such species can directly traverse the fiber body through the fiber body material to reach transduction elements internal to the fiber. Alternatively, the fiber can be configured with ports, inlets, apertures, hollow cores, or other features to provide a physical site for species entry into the fiber.

For example, an intake conduit, or microcapillary, can be provided in any suitable geometry, e.g., generally circular, rectangular or square, or other geometry, and any suitable number of distinct, separate microcapillaries can be included in a single fiber, e.g., in a selected array of intake microcapillaries. Such microcapillaries can be formed as hollow regions in a fiber cladding material, e.g., as a hollow fiber core, or can be provided as tubes or other microcapillary structures that are introduced into regions of the fiber cladding material. Each microcapillary included in a single sensor fiber can have a cross-sectional geometry and cross-sectional extent that is the same as that of one or more other included microcapillaries and/or that is different than that of one or more other included microcapillaries. Each included microcapillary preferably extends the entire length of the fiber and is preferably open and unobstructed at at least one end of the fiber, to enable intake of an analyte and species, e.g., in gaseous or liquid form. The end of the fiber therefore is appropriately arranged with connectors, seals, valves, and other mechanical apparatus, as required, to enable connection to a reservoir of intake species.

Figure 3:
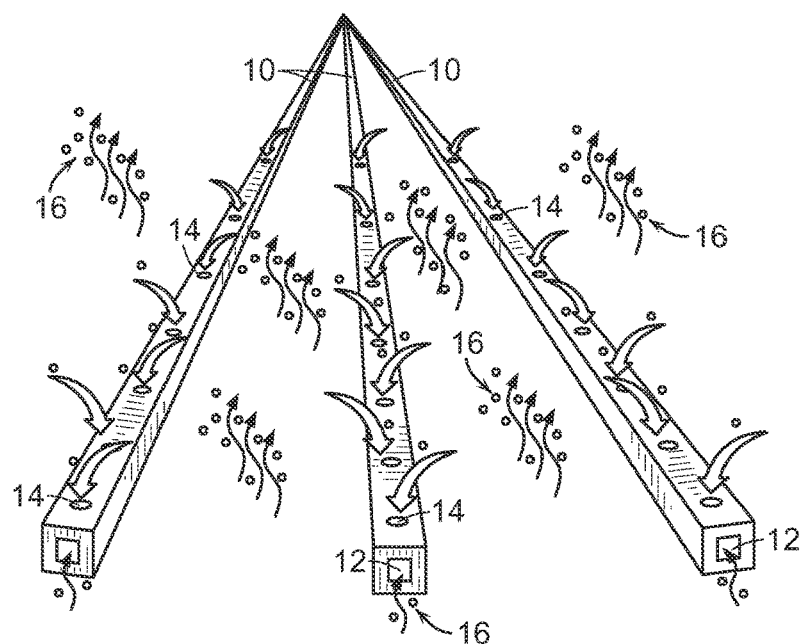
FIG. 3 is a schematic perspective view of a plurality of sensor fibers each including intake apertures along the fiber length for enabling distributed sensing.

As explained above, there can also be provided, along the length of the fiber, one or more intake apertures in the fiber wall, producing unobstructed flow paths from the local environment of the fiber to a conduit within the fiber at points along the fiber length. Referring to the schematic perspective view of FIG. 3, with such intake apertures, one or more sensor fibers 10 can be immersed, submerged, or otherwise exposed to a sensing environment to enable intake of a species 16 or analyte into the microcapillary 12 at ends of the fiber and/or at intake apertures 14 along the fiber length. This enables a distributed sensing arrangement that can be employed for detecting location of an intake species.

In fluidic communication with each fiber microcapillary, e.g., within the microcapillary itself, there is provided at least one transduction element, shown in the example arrangement of FIG. 1B as a sensing material layer 18. The fiber configuration provides a geometric arrangement such that the transduction element sensing material is exposed to species that have been taken into a fiber conduit. As explained above, for many applications, in one example, a chemiluminescent material can be employed for implementing a sensing material. With a chemiluminescent sensing material, reaction illumination is directly and locally chemically generated when the chemiluminescent material reacts with a corresponding intake species, and no excitation source is required, thereby eliminating the need to filter out excitation illumination from detection illumination. For many chemiluminescent materials, the luminescence that is produced by reaction with an intake species is isotropically emitted, i.e., the luminescence is omnidirectional. It can therefore be preferred to provide a microcapillary or other fiber structure that enables the photoconducting element 26 to capture as much of the solid angle of the omnidirectional chemiluminescence as possible.

In one example sensor fiber arrangement, like that shown in FIG. 1B, the transduction element sensing material is provided as a sensing material layer that is disposed on the wall of the fiber microcapillary. In this implementation, the sensing material layer can blanket-cover the entire circumference of a microcapillary wall surface, along a portion of the fiber length or preferably along the entire fiber length, or can cover a selected portion or portions of the fiber microcapillary wall. The sensing material layer need not be continuous along the length of the fiber, but such can be preferred to enable distributed reaction and sensing. Alternatively, the sensing material layer can be provided at a region of the fiber length at or near to the end of the fiber at which intake of a species is enabled or at sites along the fiber at which intake apertures are provided. There can be provided a plurality of different sensing material elements along the length of the fiber, with each different sensing element being positioned at a selected portion or portions of the fiber length, and each different sensing element producing illumination indicative of a different intake species or a different characteristic of a given intake species. With this configuration, a species that is taken into a fiber conduit can react with at least one, and perhaps a plurality, of sensing elements, to provide a range of detection information about the species.

The transduction element can be provided in any suitable geometry, and need not be provided as a sensing material layer. For example, the transduction element can be provided as one or a plurality of rods, strands, or other elements. Such elements can be positioned at sites within and at the surface of the sensor fiber. Transduction elements can be positioned directly within one or more fiber microcapillaries, e.g., as an elongated element threaded through a microcapillary. Transduction elements can be embedded in a wall of the fiber, e.g., arranged in the fiber cladding, or other suitable geometry, for example, coating a bundle of thinner fibers or threads that are disposed in a hollow microcapillary of the fiber.

For example, in a transduction arrangement that is alternative to that of a chemiluminescent sensing material, which luminesces upon interaction with an intake species, there can be provided a transduction fiber element that includes a fluorescent material having a quiescent level of fluorescence that is quenched upon interaction with an intake species. In this example arrangement, a hollow core or microcapillary of the fiber is configured such that the wall of the microcapillary includes a concentric one dimensional photonic band gap (PBG) structure that is in resonance with a frequency of optical pumping of the fluorescent material that is provided at the sensor fiber to produce the quiescent fluorescence. Because the pumping frequency is in resonance with the PBG structure of the microcapillary, the pumping frequency is filtered from the sensing illumination by the photodetector. The photodetector here detects only the fluorescence escaping the microcapillary wall, since the fluorescence is at longer wavelength than the pumping frequency and is off-resonance with the PBG structure. When the fluorescent material interacts with a species, the fluorescence can be quenched, and such quenching is detected by the photodetector. Thus, the transduction element can be configured as a structure, such as a PBG structure, as well as material for producing an optical indication of interaction with an intake species.

For many applications, it can be preferable to maximize the exposed surface area of the transduction element, to maximize the potential for interaction between an intake species and the transduction element, for enhancing the species detection signal. The transduction element morphology, arrangement, and geometry within the fiber can all be manipulated for this purpose. For example, there can be employed a porous transduction element having a reactive surface throughout the porous geometry.

Thus, the transduction element can be configured as a bulk material, as an optical structure and corresponding material, as a coating or layer that is disposed on a support structure that itself is not necessarily reactive, or as a layer or coating on a fiber element, such as the wall of a fiber microcapillary. The transduction element material and configuration can therefore be tailored for a wide range of applications to meet the sensitivity and other performance requirements of the applications. For example, the transduction element can be a material structure that is sensitive to optical, acoustic, or chemical stimuli, e.g., employing an acousto-optic structure or material that is sensitive to interaction with selected particles, electromagnetic radiation, or other species that can stimulate generation or control of illumination from the transduction element.

The elongated nature of the sensor fiber lends the fiber to applications in which remote and distributed sensing configurations can be preferred, and the transduction element material accordingly can be selected for such applications. For example, the sensing material can be provided with a composition that is sensitive to species that are associated with explosives, such as liquid peroxide, 2,4,6-trinitrotoluene (TNT), pentaerythritol tetranitrate (PETN), cyclotrimethylenetrinitramine (RDX), and other species associated with explosives or hazardous material.

For example, for TNT detection, a hollow core photonic bandgap fiber that is coated with fluorescent material can be disposed in a microcapillary of the sensor fiber. The bandgap of the PBG fiber is set such that it guides a fluorescor-pumping frequency, blue, and allows to escape from its wall the fluorescence, green, which is off-bandgap. This escaped fluorescence is detected by the photodetectors in the sensor fiber. Intake of TNT into PBG fiber results in quenching the fluorescence. Here, as explained in general above, the fluorescent material is optically pumped and the pumping frequency should be filtered from detection by the photodetector. Thus the transduction element can be configured to control an optical signal, e.g., by quenching the signal, to indicate interaction with an intake species.

The transduction element further can be provided with a composition that is sensitive to species that are associated with nuclear materials or radiological sources; species emitted from such sources can include, e.g., electromagnetic radiation, such as gamma radiation, particles, such as neutrons, or combinations thereof. The sensing fiber thereby can be configured as a radiation detector and/or neutron detector, e.g., by incorporating scintillator material in one or more microcapillaries of the sensor fiber. Here, when the scintillator material is excited by ionized radiation, the photoconducting material and photodetector circuits detect the resulting scintillation.

Examples of transduction element materials that can be employed in the sensor fiber include, e.g., the materials that are described in U.S. Pat. No. 7,799,573, entitled, "Detection of Explosives and Other Species," issued Sep. 21, 2010; the materials described in U.S. Pat. No. 7,208,122, entitled, "Emissive Polymers and Devices Incorporating These Polymers," issued Apr. 24, 2007; the materials described in U.S. Pat. No. 7,964,022, entitled, "Method and Apparatus for Selective Capture of Gas Phase Analytes Using Metal O-Diketonate Polymers," issued Jun. 21, 2011; the materials described in U.S. Pat. No. 7,041,910, entitled, "Emissive, High Charge Transport Polymers," issued May 9, 2006; the materials described in U.S. Pat. No. 7,759,127, entitled, "Organic Materials Able to Detect Analytes," issued Jul. 20, 2010, and the materials described in U.S. Pat. No. 7,462,325, entitled, "Luminescent Polymer Particles," issued Dec. 9, 2008; the entirety of each of these identified patents is hereby incorporated by reference.

In the sensor fiber, in optical communication with the transduction element there are disposed photoconducting elements of one or more photodetectors which are positioned within the fiber to capture illumination in the fiber that is emitted from the transduction element during interaction or reaction with an intake species. As described above with regard to FIGS. 1-2, in one example configuration of such, each photodetector is arranged with a photoconducting material element 26 disposed in the fiber in the vicinity of the transduction element. For example, the photoconducting material element can be disposed directly adjacent to a transduction element sensing material 18 or as shown in FIG. 1B, can be separated from a transduction element sensing material 18 by other fiber materials or elements, e.g., a fiber cladding material 20. If a fiber cladding material or other fiber element physically separates a transduction element sensing material 18 from a photoconducting material element 26 within the fiber, it is preferred that the fiber cladding material or fiber element be transparent to the illumination produced by the transduction element sensing material during a with an intake species, so that the illumination can propagate from the sensing material to the photoconducting material in the fiber. In general, it can be preferred that the photodetector arrangement be optimized to maximize the azimuthal numerical aperture of the detector, in order to collect as much of the transduction illumination signal as possible, for applications in which the transduction illumination is isotropically emitted.

The photoconducting material element is selected based on several considerations, including thermal fiber drawing conditions, as explained in detail below. The photoconducting material element composition is also selected based on the wavelength of illumination that is produced by a given transduction element for a selected intake species to be detected. For example, for the detection of peroxide vapor, there can be employed a transduction element sensing material formed with the components of oximide powder, phthalate powder, toluene with fluorescein, and TBAH, as explained in detail below. The wavelength of chemiluminescence that is produced by a reaction between peroxide vapor and this chemiluminescent material is centered at about 532 nm. The chalcogenide glass $Se_{97}S_3$ can absorb radiation at this wavelength, having a bandgap energy of about 1.74 eV, when crystallized, to produce a photocurrent corresponding to the absorbed illumination, and therefore is an example photoconducting material that can be employed with a chemiluminescent material that produces fluorescein emission in a sensor fiber. A wide range of semiconducting materials can be employed as photoconducting material elements.

For many applications, it can be preferred that the photoconducting material have a bandgap structure, such as a semiconductor band gap, and that the band gap be characterized by a bandgap energy that inherently enables hole and electron charge generation and corresponding photocurrent generation in response to incident illumination without specialized processing such as a dye application. A semiconductor having a band gap of less than about 3 eV, or more particularly less than about 2.5 eV or 2 eV can therefore be preferred. In general, the photoconducting material bandgap should correspond to the fluorophore emission or other expected emission to be detected. For example, $As_{24}S_{38}Se_{38}$ is characterized by a bandgap of 1.67 eV. With this bandgap, $As_{24}S_{38}Se_{38}$ is a suitable photoconducting material for operation with a fluorophore having significant emission at 742 nm, such as naphthofluorescein for instance, but $As_{24}S_{38}Se_{38}$ does not sense green fluorescein emission. The chalcogenide glass $Se_{97}S_3$ can absorb illumination at a wavelength of about 532 nm, having a bandgap energy of about 1.74 eV, and therefore can sense fluorescein emission. Thus, a single sensor fiber can enable multiple-species sensing in single fiber with the inclusion of different transduction elements and photoconducting materials. Further, the semiconducting property of the photoconducting material is preferably homogeneous and continuous along a given line and not in a composite or matrix form. With these characteristics, the semiconducting photoconducting element can be provided in a selected geometry and configuration within the fiber while producing photogenerated charge.

Pairs of example complementary chemiluminescent materials and photoconducting materials are given in Table I below.

TABLE I

| Photoconducting Glass | Fluorophore sensing material | Emission range of fluorophor and absorption range of glass |
|---|---|---|
| $As_{24}S_{38}Se_{38}$ | naphthofluorescein | red |
| $Se_{97}S_3$ | fluorescein | green |
| $As_{30}Se_{63}Sb_4Sn_3$ | Alexa Fluor ® 750 | Near infrared |

The photoconducting material is arranged in electrical communication with an electrically conductive material for collecting electrical charge that is generated by the photoconducting material in response to absorption of illumination from the transduction element. The electrically conducting material can be provided as one or a plurality of electrically conductive electrodes that are located in electrical communication, i.e., electrical contact, with the photoconducting material, and can be in direct physical contact with the photoconducting material or electrically connected to the photoconducting material through one or more electrically conductive elements disposed within the fiber.

The photoconducting material is preferably arranged in a geometry that optimizes the photodetector performance. For example, the relatively small photocurrent signal that results from chemiluminescent emission must be greater than the electrical noise current level that is characteristic of the photodetector arrangement to enable signal detection. For weak signals, the electrical noise current level is proportional to the square root of electrical dark current. To minimize dark current and enhance signal-to-noise ratio (SNR), the aspect ratio of each photoconducting element can be maximized, given that the electrical dark conductance of the photodetector scales inversely with thickness of the photoconducting material and that a larger photoconducting material area increases azimuthal numerical aperture of the photodetector.

Any number of photodetectors can be included in the fiber in any suitable arrangement. If n identical photodetectors in the fiber are electrically connected in parallel, both the electrical current they produce under illumination, $I_{bright}$, and the electrically current that is unavoidably produced in darkness, $I_{dark}$, scale linearly with n. However, the electrical noise of the signal only grows as $\sqrt{I_{dark}} \propto \sqrt{n}$, while the signal $I_{bright} - I_{dark}$ grows as n. Therefore the signal-to-noise ratio (SNR) scales as $\sqrt{n}$. As a result, for many applications, it can be preferred to integrate multiple independent photodetectors into one sensing fiber.

For many sensing materials, the illumination that is produced by, e.g., a chemical reaction at the transduction element, is isotropic, and therefore it can be preferred to capture illumination from the transduction element in a range of emission angles. The photoconducting element can be provided in the fiber in any suitable configuration that enables such. Indeed, the photoconducting element can be a layer, a coating, or other configuration within the fiber, such as a continuous layer around the circumference of the fiber, with a plurality of spaced-apart connections to a plurality of pairs of electrodes. Such photoconducting material element configurations and photodetector configurations are described in U.S. Pat. No. 7,292,758, "Optoelectronic Fiber Photodetector," issued Nov. 6, 2007, the entirety of which is hereby incorporated by reference.

Photodetector electrodes, like the electrode pairs 28 shown in the example of FIGS. 1-2, can be provided for each photodetector and can extend the entire length of the fiber, to enable transmission of an electrical sensing signal from the fiber to a circuit that is external to the fiber. The photodetector electrodes can be provided as electrically conducting layers or rods, strands, or other geometry, preferably of sufficient thickness to achieve meaningful electrical conduction at reasonable applied voltage biases. Recall that the resistance, R, in ohms, of an electrical conductor is proportional to the conductor resistivity, ρ, and length, l, and is inversely proportional to the conductor cross sectional area, A, as $R = \rho l/A$. Thus if an electrical potential difference is applied across a metal layer of the fiber in the radial direction, for radial conduction, a very thin metal layer can be sufficient to conduct large currents, while if conduction is to be in the axial direction, along the fiber length, then a metal layer as thick as 25 microns can be required for reasonable conduction along, e.g., a 10 m fiber section. In general, whatever conductor configuration is selected, it preferably is characterized by a resistance per unit length of less than about 1 KΩ/cm to enable effective electronic conduction. Various conducting material compositions and geometric combinations can be employed to tailor the conducting properties for a given application.

In addition to the photodetector elements of the fiber, there can be included additional elements for a range of fiber functionality. For example, fiber features can be included to enable all of optical transmission, electrical transmission, and optoelectronic device operation, such as photodetector operation, or other transduction or signal generation operation. Because the fiber configuration enables isolated arrangement of selected materials as well as intimate contact between materials, optical and electrical transmission can occur simultaneously yet separately, and in parallel with optoelectronic device operation. The materials selected for various fiber elements can be customized for a given application, with conductor-semiconductor, conductor-insulator, and semiconductor-insulator interfaces occurring throughout the fiber cross section and around the fiber circumference.

The direction of electrical sensing signal transmission from photodetectors in the fiber can coincide with or be counter to a direction of optical transmission through the fiber, if such is also accommodated by the fiber geometry. In general, the direction of electron and photon transmission can be longitudinal, i.e., along the fiber axial length, and/or radial, from a center region radially outward or from an outward region radially inward. The thicknesses of the materials included in a given fiber configuration are therefore preferably selected based on the particular fiber application and the desired direction of electronic and photonic transmission.

As explained above, various elements and features of the fiber can be produced by drawing a fiber preform into the fiber. Additional elements and features can then be introduced to the fiber after completion of the thermal fiber drawing process. As a result, the fiber preform does not need to include every element of the final fiber configuration; various fiber features can be produced from fiber preform elements and various fiber features can be produced with elements and materials incorporated into the drawn fiber. All of the microcapillary, sensing element, and photodetectors can be included in a fiber preform, or alternatively, a subset of elements, such as the microcapillary and photodetectors, can be included. For those fiber elements that are produced by thermally drawing a fiber preform, selected materials are assembled in a macroscopic fiber preform and then thermally drawn to a final fiber geometry. Additional fiber elements and materials can then be incorporated into the fiber arrangement.

The thermal deformation conditions inherent in the thermal fiber drawing process require that the fiber preform materials, including those conducting, semiconducting, and insulating materials selected for a given fiber configuration, be compatible for co-drawing. In general, this co-drawing compatibility can be specified as a condition of compatible viscosities at the fiber drawing temperatures of interest. More specifically, the materials should be above their respective softening points at an overlapping draw temperature to enable their co-drawing. Precise viscosity matching between fiber materials is not required; specifically, the materials need not have the same viscosity at the draw temperature, but rather all should flow at that common temperature. It is further understood that for some material combinations, high viscosity in one or more materials that comprise the majority of the volume of the fiber preform is sufficient to enable structural integrity of all co-drawn materials. Suitable materials additionally are preferably characterized by good surface adhesion and wetting in the viscous and solid states without cracking even when subjected to thermal quenching. For many applications and thermal drawing processes, compatible materials are described as those in which the viscosity of each element in the fiber preform is less than about $10^8$ Poise, or preferably less than about $10^6$ Poise, at a common fiber draw temperature, and metals being molten at the common fiber draw temperature, and with the properties of the materials, such as electrical conductivity, and material integrity, being preserved during the thermal drawing process. With this requirement, it can be expected that not all fiber elements can be produced by thermal drawing from a preform, and some fiber elements can be incorporated after thermal drawing. Alternatively, there can be selected materials and configurations that enable all of the sensor fiber elements to be produced by a single thermal fiber drawing step.

In general, it is recognized that materials that are amorphous and glassy are particularly well suited to be thermally drawn from a preform into a fiber structure. The term amorphous here refers to a material morphology that is a continuous atomic network in which there is no repeating unit cell or crystalline order; a glassy material typically is not easily crystallized at high processing temperatures. For many applications, it can be preferred to select semiconducting and insulating fiber materials that are glassy to enable fiber drawing at a reasonable speed while self-maintaining structural integrity and regularity. Such can be achieved with glassy materials because the viscosity of a glassy material varies quasi-continuously between solid and liquid states, in contrast to a crystalline material. By employing a glassy material, it is ensured that the fiber structure will remain amorphous, i.e., not crystallize, when cycled through softening and drawing temperatures.

Amorphous thermoplastic polymeric insulating materials are particularly well-suited to a fiber co-drawing process for producing electrically insulating regions of the fiber as well as a fiber cladding material and an outer fiber surface. The insulating material is preferably transparent to a selected wavelength or band of wavelengths for which the fiber photodetectors are configured if the insulating material is disposed along a path of illumination to the photoconducting material. High glass-transition-temperature polymeric insulators are an example of such; a wide variety of amorphous high glass-transition-temperature polymer materials are available and can be processed with a range of techniques to form various material configurations that are characterized by excellent mechanical toughness. Examples of thermoplastics that can be employed include poly-ether imide (PEI), poly-sulfone (PS), poly-ether ether ketone (PEEK), polycarbonate (PC), and poly-ether sulfone (PES).

There also can be employed, as an insulating material, liquid crystal polymers (LCP's), low glass transition polymers such as poly-methyl methacrylate (PMMA), polycarbonate (PC), poly-ethylene (PE) and other such thermoplastic polymers. Poly-tetrafluoroethylene (PTFE or Teflon™) and other fluorinated polymers or copolymers can also be employed in configurations in which their characteristically poor surface adhesion properties can be accommodated. While it is preferred that amorphous polymer materials be employed, it is also recognized that some semicrystalline polymers, e.g., branched PTFE, can be employed. A necessary condition for any suitable polymeric material is that there exist a fiber draw temperature at which the polymer can be drawn into a fiber at a reasonable speed, e.g., greater than about 1 mm/minute, without decomposition.

As explained above, if one or more elements of the sensor fiber photodetector structure is implemented by thermal drawing of a preform, then each is considered for their compatibility with the drawing process. For example, the photoconducting material is selected based on an ability to thermally draw the photoconducting material into the fiber arrangement. For many applications, an amorphous semiconductor can be employed as the photoconducting material, and are particularly well-suited, given their low glass transition temperatures and stability with respect to oxidation. Amorphous semiconductors are also preferred for their good wetting properties, defined by the contact angle between the semiconductor and polymer materials at the draw temperature; a contact angle of less than about 150 degrees can be preferred. Further, amorphous semiconductors generally are characterized by a viscosity value that is similar to that of the polymers described above at polymer draw temperatures. Both organic semiconductors, such as PPV, or poly thiophene, as well as inorganic semiconducting materials can be employed.

The class of semiconducting chalcogenide glasses are particularly well-suited to a fiber co-drawing process. Chalcogenides are high-index inorganic glasses that contain one or more of the chalcogen elements of sulfur, selenium, and tellurium. In addition to the chalcogen element, chalcogenide glasses can include one or more of the following elements: boron, aluminum, silicon, phosphorus, sulfur, gallium, germanium, arsenic, indium, tin, antimony, lithium, thallium, lead, bismuth, cadmium, lanthanum, and the halides fluorine, chlorine, bromide, and iodine. There is a very wide variety of different compositions within the family of chalcogenide glasses and thus the properties of a given composition can be tailored through compositional adjustment.

For the photoconducting element of the sensing fiber photodetectors, the chalcogenide glasses including arsenic and selenium, e.g., $As_{40}Se_{60}$ or $(As_{40}Se_{60})_{1-x}Sn_x$, can be employed to obtain a desired photoconducting characteristic for a range of chemiluminescent radiation wavelengths. Similarly, glasses in the arsenic-selenium-tellurium ternary systems, such as $As_{40}Se_{54}Te_6$ and $Se_{97}S_3$, can be tailored for a selected chemiluminescent radiation system. $Se_{97}S_3$ is particularly well-suited for detecting fluorescein emission, and thermally draws well into a fiber structure in thin sheets without undergoing capillary break up. $Se_{97}S_3$ is characterized by a glass transition temperature that enables co-drawing with fiber polymer cladding materials, such as polysulfone, with fiber conductive polymer pads and other elements, such as conductive polycarbonate, and with fiber metal electrodes, such as eutectic tin-lead. $Se_{97}S_3$ therefore is particularly well-suited as an in-fiber photoconducting element.

It is to be recognized that a wide range of polymers can be paired for co-drawing with a chalcogenide material; e.g., both high and low glass-transition-temperature polymers can be employed in conjunction with low glass transition chalcogenide glasses. As a result, there can be implemented a wide range of fiber materials that are produced from a fiber preform and that are thermomechanically compatible for codrawing into a fiber. For example, as explained above, the chalcogenide glass $Se_{97}S_3$ has a band gap energy of 1.74 eV, when crystallized, that corresponds to the central wavelength of 532 nm emitted by a peroxide-reactive sensing material. $Se_{97}S_3$ is therefore well-suited as a photoconducting material for peroxide sensing. Amorphous $Se_{97}S_3$ is thermomechanically compatible with polysulfone (PSU), and therefore the two materials can be co-drawn and the $Se_{97}S_3$ crystallized after thermal drawing, in the manner described below, for a peroxide sensor fiber.

There can be produced electrically conducting elements, e.g., configured for the photodetector electrodes of the sensing fiber, by thermal co-drawing of an electrically conducting material with, e.g., photoconducting materials and insulating materials. At a selected fiber draw temperature, the selected conducting material should be molten or sufficiently ductile to enable thermal deformation. For many applications, it can be preferred to employ an electrically conducting material having a melting temperature that is below a desired fiber draw temperature. It additionally is preferred that the conducting material sufficiently wet the surfaces of adjacent materials such that the contact angle between the conducting material and these materials is less than about 150 degrees, at the fiber draw temperature, for the case of a bare-surfaced conducting material, without inclusion of an adhesion promoter.

Given a selection of a high glass-transition-temperature polymeric insulating material and a chalcogenide semiconducting material to be co-drawn into elements of the sensor fiber, a low melting-temperature metal or metal alloy can be a preferable conducting material selection. For example, tin, indium, bismuth, cadmium, lithium, or other low melting-temperature metal is particularly well suited for the material trio, as well as Sn-based or other selected alloys. In addition, a selected metal alloy can be synthesized to provide desired melting temperature, electrical conductivity, and other properties. For example, Sn—Ag, Sn—Sb, Sn—Cu, $Sn_{85}Zn_{15}$, $Bn_{58}Sn_{42}$, and other alloys can be employed. Further, there can be employed suitable amorphous glassy metals, or other suitable metal composition. For example, it can be preferred for some applications to control the surface roughness and other surface factors in the fiber preform arrangement, and to do so, there can be included various material layers, such as conductive polymer layers and pads. Such materials can be included in a fiber preform to decrease cross-sectional discontinuity of interfacial tension and viscosity at the interface between electrically insulating and electrically conducting regions. Conductive polymers such as conductive polycarbonate (CPC) and conductive polyethylene (CPE) are examples of such materials.

The transduction element can be co-drawn with other fiber elements from a fiber preform into the sensor fiber, so long as the transduction material does not decompose at a selected draw temperature. A wide range of transduction element sensing materials and structures, including fluorescent PBG structures, can therefore be co-drawn from a preform into a fiber. For example, the chemiluminescent material described above based on a mixture of oximide powder, phthalate powder, toluene containing fluorescein and TBAH can be prepared and provided as a coating, layer, or other arrangement in a fiber preform for co-drawing into a sensor fiber. Other transduction elements and sensing materials can be included in a fiber preform for co-drawing as-desired for a given application.

With these considerations and material examples, it is to be understood that some experimental verification can be required to confirm the co-drawing compatibility of various candidate fiber materials. Once the thermal drawing temperature of each material of interest is determined, and assuming that the materials can be thermally drawn within a common temperature range, it can be prudent to examine the viscosities of the materials across the selected drawing temperature range to ensure that the viscosities are compatible. As stated above, it is not required that the viscosities of the various materials be the same at the fiber draw temperature, but rather that all materials should at least flow at the draw temperature, with conducting materials preferably molten at the draw temperature. Also, as stated previously, it is understood that it can be preferred that the material which comprises the majority of the volume of the fiber preform be characterized by the highest viscosity.

With the fiber preform materials selected, assembly of materials into a fiber preform is carried out employing processes that are compatible with the selected materials to produce desired material configurations based on the considerations described above. No particular preform assembly technique is required by the invention. Rather, a range of techniques can be employed to produce a preform having a configuration corresponding to the desired post-draw fiber. In accordance with the invention a variety of preform elements can be provided and/or produced separately for incorporation together into a preform arrangement. Considering first electrically conductive materials, commercially available rods, strands, foils, sheets, and other articles of conducting material can be employed. Thermal evaporation, E-beam evaporation, sputtering, chemical vapor deposition (CVD) and other physical deposition techniques can be employed for coating preform elements with a conducting material layer or layers. It is to be recognized, however, that depending on a particularly selected deposition technique and the deposition parameters, not all deposited films may be compatible with a fiber co-drawing process; e.g., the deposited conducting material must be sufficiently thick as well as ductile to accommodate the drawing process.

Whatever conducting material geometry is employed, if the conducting material is a metal or metal alloy that will melt at fiber draw temperatures, then the metal or alloy is preferably arranged in the preform such that the metal or alloy is confined geometrically by materials such as the fiber cladding material, in the preform, that will not melt at the draw temperatures. This metal confinement ensures that the draw process retains the desired metal configuration in the fiber even while the metal is in a fluid state.

In addition, it is recognized that electrically conducting materials can oxidize readily at elevated temperatures, including preform consolidation and fiber draw temperatures. Oxidized conducting materials may not melt or may flow nonuniformly, resulting in nonuniform or even inoperable conducting elements in the drawn fiber. To eliminate this condition, it can be preferred to inhibit and/or remove oxide from conducting element surfaces for various preform geometries.

To inhibit such oxidation, an antioxidizing, or oxide inhibiting, agent that preferably is a surface wetting promoter can be incorporated into the preform at interfaces surrounding the conducting material, e.g., surrounding metal elements in the preform. This can be achieved by, e.g., physically applying an oxidation inhibitor to the conducting material surfaces during the preform assembly. A particularly well-suited oxidation inhibitor is a flux; fluxes in general are synthetic carboxylic acid-containing fluids or natural rosin fluxes. These compounds serve to enhance and promote the wetting of the preform materials by the metal or other conducting material so as to prevent capillary breakup of the conducting material. This enables the use of conducting materials that may not normally exhibit the required surface wetting condition. Example suitable fluxes include Superior No. 312 flux, or Superior 340 flux, both from Superior Flux and Mfg. Co., Cleveland, Ohio. The flux can be applied directly to the conducting material surfaces, and can alternatively or in addition be applied to surfaces of other materials that in the preform configuration are to be adjacent to conducting material surfaces.

In a further technique for inhibiting oxidized conducting elements in a drawn fiber, an oxidation inhibitor can be applied to one or more preform elements by adding it to the elements. For example, an oxidation inhibitor can be added to a polymer material that is to be located adjacent to a conducting material element. The oxidation inhibitor constituent preferably segregates to or is naturally located at the surface of the polymer for application interaction with adjacent conducting materials. Alternatively, a polymer, semiconductor, or other material that itself has oxidation inhibition or oxide growth suppression properties can be selected for use in the preform adjacent to conducting elements. Oxidation inhibiting and/or growth suppression buffer layer materials can also be included between a conducting element and an adjacent material. Whatever oxidation inhibition technique is employed, it is preferred that the oxide inhibitor does not decompose at the preform consolidation temperature or the fiber draw temperature.

Considering insulating fiber preform elements, due to the relative ease of preform assembly and drawing of polymer materials, compared with other glassy insulating materials, polymeric insulating materials can be preferred for many fiber applications. Polymeric insulating materials can be readily obtained commercially or produced in a desired configuration. For example, commercially available polymer rods, tubes, sheets, and films from, e.g., Westlake Plastics Co., Aston, Pa., can be employed. Polymer rods and tubes can also be produced by thermal consolidation of a rolled polymer film. Polymer layers can be produced by chemical vapor deposition techniques such as plasma enhanced chemical vapor deposition, by spin-coating, dip-coating, as described above, by roll-casting, extrusion, and other techniques. Liquid polymer can be applied, as described above, for coating preform core materials, strands, wires, rods, layers of other material, and preform elements.

Similarly, chemical and physical deposition techniques can be employed for producing amorphous semiconducting material preform elements. As explained above, for many applications, chalcogenide glass semiconductors can be preferred for their co-drawing compatibility with polymeric insulators. Rods, tubes, sheets, films, and other semiconducting structures can be employed in the fiber preform. A wide range of semiconducting glass structures can be obtained commercially, e.g., from Alfa Aesar, Ward Hill, Mass., and also can be synthesized as a particularly desired composition and geometry.

For example, in accordance with the invention, chalcogenide glass structures can be chemically synthesized using sealed-ampoule melt quenching techniques. In one example scenario, pure elements such as As and Se are placed in a quartz tube under a nitrogen atmosphere. The tube is initially maintained open at one end. A vacuum line is connected to the open end of the tube and the tube is preheated under vacuum to melt the elements and remove trapped gasses and surface oxide. Heating to 330° C. for one hour at a heating ramp rate of about 1° C./min and thereafter cooling to room temperature at a ramp down rate of 1° C./min is sufficient. An oxygen gettering agent such as Mg can be added to the tube to reduce the partial pressure of oxygen within the tube.

The tube is then sealed under a vacuum of, e.g., $10^{-5}$ Torr, using, e.g., a high-temperature torch. The sealed tube is then heated in a rocking furnace for physically mixing the elements during a prescribed heating schedule corresponding to the elements included. For example, the As—Se mixture can be heated to 800° C. at a rate of about 2° C./min, while held vertical, for twenty four hours, and then rocked for six hours to increase mixing and homogenization. The glass liquid is then cooled, e.g., to 600° C., in the furnace, and then quenched in water. Subsequently, the mixture is annealed for one half hour to the glass transition temperature, e.g., about 180° C., before being cooled gradually to room temperature. Using this synthesis technique, mechanically strong semiconducting structures can be fabricated as, e.g., rods, tubes, and other structures. Once the glass is synthesized, it is no longer sensitive to oxygen at room temperature. It therefore can easily be handled in ambient atmosphere for incorporation into a preform or employed for further processing.

In addition to conducting, semiconducting, and insulating preform elements, sacrificial elements can be included in a preform to aid in defining a preform shape, and then removed prior to drawing of the preform into a fiber. For example, quartz or Teflon™ tubes or rods can be included in a preform at locations for which a hole is desired, and then chemically etched away or mechanically removed after consolidation of the preform. This technique provides a particularly elegant method for defining gaps and spaces in a preform assembly prior to fiber drawing.

For many applications, where a high glass-transition-temperature polymer is employed as a photoconducting material, it can be particularly advantageous to employ layers of polymer material in assembly of a preform structure. For example, for the photoconducting material of the fiber photodetector, alternating layers of semiconducting and insulating materials can be produced by depositing a semiconductor layer on one or both sides of a polymer film or piece and configuring the film into a selected geometry. Deposition of a semiconductor layer on one or both sides of a polymer film can be accomplished by thermal evaporation, chemical vapor deposition, sputtering, or other suitable deposition technique. Where a semiconductor such as a chalcogenide glass has been synthesized, e.g., by the chemical synthesis process described above, conventional thermal evaporation of a synthesized source material onto a polymer film can be a particularly convenient deposition technique. It is preferred that the polymer film be highly uniform in surface quality and thickness and be cleaned, e.g., with an alcohol, prior to the deposition process. Thermal evaporation can be carried out with conventional hot filament evaporation techniques, preferably at a pressure below, e.g., about $10^{-4}$ Torr. A conventional vacuum evaporator, e.g., a Ladd Research Industries Model 30000, can be employed. If desired, both sides of a polymer film can be coated with a selected material. In order to assemble a layered preform structure of the polymer film and a material deposited on the film in the manner just described, the coated polymer film can be wrapped, or rolled, around a mandrel or other preform structure a number of times to produce a desired number of layers.

The photodetector electrodes can be formed in conjunction with the polymer film using, e.g., tin foil, of a desired thickness, e.g., between about 25 µm and about 1 mm in thickness. Suitable foils can be commercially obtained, e.g., from Goodfellow Corporation, Devon, Pa., or can be produced by, e.g., pressing a metal rod to the desired foil thickness. The foil is preferably cleaned and dried in the manner of the polymer film. Additionally, it can be preferred to coat the foil with an oxide inhibitor, e.g., a flux, as described above. Alternatively, the electrodes can be formed as layers or material that are deposited in the manner described above.

In addition to the preform assembly techniques described above, the preform materials can be drilled, casted, molded, or otherwise shaped for producing a preform. For example, holes can be drilled in a polymer body and conducting or semiconducting strands or other elements fitted into the drilled regions. Any preform assembly technique that accommodates all of conducting, semiconducting and insulating materials in an arrangement that enables co-drawing of the three materials can be employed.

Depending on the selected preform assembly technique and resulting arrangement, it can be preferred to thermally consolidate an assembled preform prior to the fiber drawing process. Consolidation is a process whereby under heat and vacuum conditions one or more of the preform materials are caused to fuse together, with air pockets in the preform being substantially eliminated. This results in a preform assembly that can produce intimate interfacial contact between adjacent material layers in the final fiber, and provides the preform with self-maintaining structural stability during the fiber draw process.

The specific conditions of the consolidation process are selected based on the particular materials incorporated into a given preform. If, e.g., a high glass-transition-temperature polymer is employed in the preform, then the consolidation temperature preferably is above the glass transition temperature of the polymer. The preform is maintained at the elevated temperature for a time sufficient to cause the polymer to fuse to adjacent elements included in the preform; the temperature is selected based on the preform diameter and its materials. Given a preform including PES polymer elements, $As_2Se_3$ semiconducting elements, and Sn metal elements, a consolidation temperature of between 250° C.-280° C., e.g., about 260° C., at a pressure of about $10^{-3}$, sufficiently consolidates the structure. For a polysulfone-based preforms, consolidation of a preform having a geometry of, e.g., about 0.75"×0.75" can be conducted, e.g., at a temperature of about 225° C. for about 30 minutes.

For most consolidation temperatures, metal preform elements will be melted during the consolidation process but confined to their intended geometries by the arrangement of confinement layers described above. Depending on the consolidation temperature, semiconducting preform elements may soften or may remain solid. The inclusion of at least one material that can fuse to adjacent materials during consolidation is all that is required. In the PES-$As_2Se_3$—Sn example given above, the consolidation temperature is set to enable softening and fusing of the PES polymer to adjacent preform elements.

It can be preferred to carry out the consolidation process in a vertical rotating zone refinement furnace. In such a furnace, the preform longitudinal axis is held vertically and a zone refining heating process is carried out along the preform length. Preferably the consolidation is conducted from the preform bottom upward through the preform to its top. The heating time for each incrementally consolidated preform section along the preform length is determined based on the preform diameter and material elements as explained above.

As explained above, in construction of a preform there can be included one or more sacrificial elements that are incorporated in the preform solely to define spaces to be provided in a final fiber geometry. For example, a mandrel, rod, or tube, or other machined geometry, can be included in a preform where a hollow fiber core or other region is desired. If a sacrificial element is included in a preform, it is preferred that the consolidation process be carried out at a temperature below the glass transition temperature of that element, so that structural integrity of the sacrificial element is maintained during the consolidation process and the preform does not collapse on itself.

For many preform material arrangements, a sacrificial element can be constructed that can withstand reasonable consolidation temperatures and pressures and can easily be removed from the preform after consolidation. For example, Teflon™ tubes, rods, or other elements can be readily incorporated into and removed from a preform. Any material that exhibits poor surface adhesion and can withstand the consolidation process is a good sacrificial element material.

It is preferable to remove the Teflon™ or other sacrificial element immediately after the consolidation process, while the preform is hot and slightly expanded. This enables ease of removal. Once the preform cools and correspondingly shrinks, it can be difficult, if not impossible, to remove the element by simple mechanical force.

Alternatively, sacrificial elements which can be removed from a consolidated preform by chemical etching can be employed. For example, glass, quartz, or other etchable materials that can withstand the consolidation process can be employed. In such a scenario, after the consolidation process, the preform is exposed to a chemical etchant that selectively attacks the sacrificial elements. For example, hydrofluoric acid or other acid bath can be employed for wet chemical etching of sacrificial elements. Dry etch techniques, e.g., plasma etch techniques, can also be employed if such can be adapted to contact and selectively attack the sacrificial materials in a preform.

Once a preform has been consolidated, if necessary, and sacrificial elements removed from the preform, drawing of the preform into a fiber can proceed. Fiber drawing can be carried out in a fiber draw tower or other suitable draw apparatus. In such an apparatus, a top preform downfeed mechanism is provided for holding an end of the preform and lowering the preform into a furnace. It can be preferred to employ a vertical draw furnace enabling three temperature zones, namely, top, middle, and bottom temperature zones. Below the furnace is provided a capstan with spooler for spooling the drawn fiber. Measurement equipment, e.g., a laser diameter monitor, from Beta LaserMike, Dayton, Ohio; fiber tension measurement devices, e.g., Model SM9649P, from Tension Measurement, Inc., of Arvada, Colo., and other monitoring equipment can be included.

The draw furnace temperature zones, preform downfeed speed, and capstan speed are selected based on the preform materials and configuration to enable co-drawing of preform conducting, semiconducting, and insulating material elements into a desired fiber configuration. The top furnace zone temperature is selected to cause the preform materials to soften but not flow. The middle furnace zone temperature is selected as the draw temperature, to cause the preform to flow into a fiber form. As explained above, the draw temperature is selected to be above the glass transition temperature of the insulating and semiconducting materials, and for most material combinations, will be above the melting temperature of the conducting material. If an excessively high draw temperature is employed, the preform will catastrophically deform, while an excessively low draw temperature will cause preform distortion and expansion. The structural arrangement of the preform must be preserved at the draw temperature.

It is therefore to be recognized that some experimental testing of draw temperatures can be required for a given preform assembly. As explained above, a reasonable criterion for polymer, metal, and chalcogenide material draw temperatures is that all materials have a viscosity lower than about $10^8$ Poise at the draw temperature and that the metal be molten at the draw temperature. Given a preform of PES polymeric insulating elements, $As_2Se_3$ semiconducting elements, and Sn conducting elements, a top zone temperature of between about 180° C.-250° C., e.g., 190° C.; a drawing zone temperature of between about 280° C.-315° C., e.g., 300° C.; and a bottom zone temperature that is unregulated, and therefore at, e.g., about 100° C., due to proximity to the draw zone, can be employed for successfully drawing the preform into a fiber. Given a preform of PS polymeric insulating cladding material, $Se_{97}S_3$ photoconducting material, and eutectic tin-lead electrical conductors, a drawing zone temperature of between about 200° C. and 300° C. can be employed, with a drawing zone temperature of about 265° C. preferred.

For many applications, it can be preferred to ensure uniform heating of the preform during the drawing process. A uniformly heated furnace employing, e.g., distributed filament heating, is particularly well suited for the drawing process. It is further preferred that the preform be maintained laterally centrally in the drawing temperature zone. If the preform temperature distribution becomes nonuniform due to lack of furnace temperature control or lateral misalignment of the preform as it passes downward through the drawing zone, there could be produced local preform regions of differing temperature and differing viscosity. Local viscosity fluctuations in the preform could produce a capillary effect in which material, particularly molten metal, flows to other preform regions, and distorts the intended fiber geometry. The physical confinement of metal elements described above can be important for inhibiting such a condition, but in general, uniform preform heating is preferred for preserving an intended fiber geometry.

The combination of preform downfeed speed and capstan drawing speed determine the diameter of fiber produced by the drawing process for a given drawing temperature. A diameter monitoring system can be configured in a feedback loop to enable control of, e.g., the capstan speed, by the diameter monitors based on a diameter setpoint and control algorithm. For the drawing furnace zone temperatures recited above for drawing a PES-$As_2Se_3$—Sn preform of 20 cm in diameter and 30 mm in length, a downfeed speed of between about 0.002 mm/sec-0.004 mm/sec and a capstan speed of between about 0.7 m/sec-3 m/sec produces a fiber of a diameter between about 1200 μm and 500 μm and a length of several hundred meters. As can be recognized, a reduction in draw speed increases the resulting fiber diameter. Within the fiber, layers of the preform are reduced in thickness by a factor of ~20-100. In accordance with the invention, a preform can be drawn multiple times to reduce the final resulting fiber geometry correspondingly.

The drawdown ratio between a fiber preform and the resulting fiber is not precise; specifically, the preform layer thickness drawdown ratio does not always correspond precisely to the fiber's outer diameter drawdown ratio. This can be due to a number of factors, including, e.g., reduction of hollow core or other hollow spaces within the preform. The relationship between the layer and outer diameter drawdown ratios is found to be closer to 1:1 for large-diameter, low-tension draw procedures. High-temperature, low-tension draw procedures can tend to produce fibers having layers thicker than predicted by the outer diameter reduction ratio, due, e.g., to partial collapse of hollow regions. It is found, however, that such effects are fairly reproducible and can be predicted based on experimental history.

Upon completion of the fiber drawing operation, there is produced a fiber that can enable transduction of energy from interaction with a species to an optical signal, optical transmission, separate and independent electrical transmission, and optoelectronic device operation. The conducting and semiconducting fiber elements therefore are provided to be functional in at least one aspect of transmission or device operation and the insulating fiber elements can be provided for electrical and/or optical isolation as well as for functionality in at least one aspect of transmission or device operation.

It is to be recognized that while it can be preferred to employ conducting, semiconducting and insulating preform materials, the fiber that results from the draw process can exhibit altered material conductivities given the scale of feature sizes and cross-sectional element dimensions of the drawn fiber. For example, the conditions of the fiber drawing and/or the structural and dimensional changes that result from the drawing could render a semiconducting or metal preform material insulating, or an insulating preform material conducting. Further, the energy band structure of materials provided in a preform can be altered by the fiber drawing and/or resulting dimensional changes, and can change their conductivity correspondingly, given the scale of fiber feature sizes. In addition, it is recognized that one or more constituents can be incorporated into preform materials that adjust the materials' conductivity upon fiber drawing. For example, conducting filaments, such as carbon fibers, can be included in a preform material such as polymer whereupon drawing, the spacing between the fibers is reduced, leading to a change in polymer conductivity.

After fiber drawing, post-draw processes can be conducted as-desired for a given application. For example, not all fiber elements, materials, and components need to be thermally drawn; after thermal drawing, additional materials and elements can be added to the fiber arrangement. In one example of such, one or more hollow microcapillaries in the drawn fiber can be coated with one or more sensing materials, along the length of a microcapillary or at selected points of the microcapillary along the fiber length. Accordingly, transduction element need not be included in the fiber preform, e.g., transduction element sensing material need not be included in the fiber preform, and can be introduced to the fiber structure after thermal drawing of the fiber.

In one example of such, in which the sensor fiber is configured to detect peroxide vapor, a peroxide sensing material is disposed in the fiber after fiber drawing. In formation of an example of such sensing material, there is produced a mixture of 2 mg of oximide powder, 2 mg of phthalate powder, 3 μl of toluene containing 1 mg/ml of fluorescein, and 10 mg/ml of TBAH. The mixture is stirred and heated at a temperature above about 90° C. to become a uniformly mixed liquid. Than the drawn sensor fiber is dipped into a vessel including the mixed liquid, whereby the liquid is taken into the hollow microcapillary of the fiber by capillary force. After intake of the liquid, there is gently blown a gas through the conduit to produce a uniform coating of, e.g., about 10 μm in thickness on the conduit walls. The fiber structure is then cooled to room temperature, whereupon the coating then becomes viscous.

There can additionally be provided various fiber elements such as optical and protective coatings and/or structures that are tailored for particular environmental conditions. For example, unlike optical transmission fibers, the photodetecting sensor fiber is not immune to electromagnetic interference. This condition can be alleviated by providing an electromagnetic barrier at the fiber for blocking particular electromagnetic radiation from reaching the photoconducting material in the fiber. Additional coatings, layers, and other fiber elements can be introduced to the fiber after fiber drawing.

Further post-draw processes can be conducted as-required for given fiber materials and arrangements. For example, many materials included in the drawn sensor fiber, such as semiconducting chalcogenide photoconducting materials, are amorphous at the time of thermal fiber drawing. Such amorphous morphology in general is characterized by a relatively low electrical conductivity and corresponding photoconducting response. In order to increase the electrical conductivity to a level that provides reasonable photoconducting response, it can be preferred for many amorphous photoconducting materials to at least partially crystallize the material after thermal fiber draw. After thermal drawing of the fiber, the entire fiber structure can be annealed, e.g., under vacuum at a suitable annealing temperature that will not damage the fiber, e.g., between about 100° C. and about 250° C., for a suitable time, ranging from minutes to days. For example, annealing of a fiber at 150° C. overnight is sufficient to crystallize a photoconducting layer of $Se_{97}S_3$. With this annealing step, amorphous photoconducting materials can be at least partially crystallized to improve their conductivity to a level that enables effective fiber photodetector operation. This improved conductivity can be dramatic; for example, the conductivity of in-fiber crystallized $Se_{97}S_3$ photoconducting material is about 8 orders of magnitude higher than in the amorphous state of the material.

It is recognized, however, that the dark current of the sensor fiber's photodetectors scales linearly with fiber length if the amorphous photoconducting material is crystallized along the entire fiber length. To circumvent the reduction in sensing sensitivity that would be associated with the increased dark current, the photoconducting material can be selectively crystallized only at selected locations, rather than along the entire fiber length. For example, the photoconducting material can be crystallized only at those axial locations where a sensing event is expected to occur. In a remote sensing application, only the last few centimeters of a fiber need be crystallized, in which case the detection sensitivity will not depend on the length of the remaining fiber segment, given the generally very large difference in electrical conductivity between amorphous and crystalline states of material.

With processing of a drawn sensor fiber complete, the fiber can be configured in any suitable arrangement for a given sensing application. The sensor fiber can be configured as a single fiber detector, or in a plurality of sensor fibers arranged in any suitable geometry. Bundles, cables, braids, and other arrangements of multiple fibers can be employed. Further, a plurality of sensor fibers can be woven, interleaved, or otherwise arranged to form a grid, a sheet, a fabric, or other large-area sensing surface, e.g., for wearable clothing, for protective structural coverings, or surface materials of machinery or other apparatus. Further, the intrinsic low profile and mechanical flexibility of the sensor fiber enables a plurality of such fibers to be embedded into extrinsic structures, such as fabric or other materials that are woven or otherwise arranged with non-fiber threads and into which sensor fibers can be woven at selected sites.

The sensor fiber further can be embedded in large scale structures, such as container linings, ship hulls, and automotive bodies. The sensor fiber further can be provided as-drawn with an extensive length, and woven in very large grids, e.g., 100's of $m^2$, to produce detector arrays that can be disposed over large physical areas and locations, e.g., embedded in large scale structures, or configured as long ribbons along extended sites or across extended stretches of physical roads or borders, providing monitoring and detection capabilities.

Each in a plurality of sensor fibers can be tailored for detecting a selected species, with the plurality of fibers arranged for multi-species detection. Any of the mechanical arrangements just described can be employed here with fibers in a group configuration for detection of more than one intake species by the fiber group. As described previously, a single sensor fiber can itself be configured for detection of multiple species with the inclusion of a plurality of different sensing materials. Thus, the sensor fiber can be arranged in a wide range of configurations, and is particularly well suited for remote and distributed sensing configurations.

Example

A hollow core rectangular preform 50 was assembled and thermally consolidated as shown in FIG. 4. The preform was arranged as two identical preform subassemblies, each including a 75 µm-thick layer 52 of polysulfone (PSU) fiber cladding material on which was evaporated, onto the laminar facet of the PSU, a 35 µm-thick layer 54 of photoconducting chalcogenide, $Se_{97}S_3$. Conductive polycarbonate (CPC) pads 56 were disposed on the outer face of the coated PSU layer, and electrodes 58 of $Sn_{63}PB_{37}$ were disposed on the CPC pads. The CPC pads were included in order to decrease cross sectional discontinuity of interfacial tension and viscosity at the transition from the insulating to the electrically conductive regions along the $Se_{97}S_3$ edge. It was determined that the thermal drawing of a thin and wide sheet of some materials, such as the $Se_{97}S_3$ chalcogenide sheet, can be complicated by a tendency of the sheet to undergo a capillary break up into thin filaments while being thermally drawn. The surface roughness of the preform materials surrounding the $Se_{97}S_3$ layer were therefore controlled to maintain continuity of the sheet during fiber drawing. The preform was accordingly designed so that only laminar polymer surfaces were in contact with the $Se_{97}S_3$ layer. The CPC pads prevented shear flow of $Se_{97}S_3$ during the draw, further improving the continuity and uniformity of the chalcogenide photoconducting material.

Two outer PSU plates 60 were machined to provided slots and trenches for encapsulating all of the components, and a flat plate 62, to be later etched, was provided on the opposing side of the structure for definition of a hollow intake microcapillary. With this design, two identical and independent photodetecting structures were incorporated into two preform subassemblies. The aspect ratio for each of the photoconducting layers was maximized in order to increase the azimuthal numerical aperture while decreasing the dark conductance of each detector, which scales inversely with the layer thickness as explained above.

To consolidate the structures and form a monolithic macroscopic preform, each of the two photodetector preform structures was separately consolidated, including the outer PSU layers. Consolidation was conducted at a temperature of 225° C. for 25 minutes. Then each PSU layer 62 for defining the hollow intake conduit was machined to form a trench, and the two preform assemblies were integrated, with a Teflon™ rod inserted in the resulting hollow conduit space produced by the machining step. The integrated assembly was then further consolidated, again at a temperature of 225° C. for 25 minutes. After this final consolidation step, the Teflon™ rod was removed.

The consolidated preform 50 was thermally drawn, as shown schematically in FIG. 5, in a draw tower having a heating zone 70 at a temperature of about ~265° C. at a stress of ~650 g/mm$^2$, to produce a sensor fiber 10 containing two independent photodetecting structures flanking opposite sides of the fiber. After the fiber draw, the fiber was annealed under vacuum at a temperature of about 150° C. for about two days in order to crystallize the $Se_{97}S_3$ layers along the full fiber length to functionalize the chalcogenide layers and improve their conductivity in the manner described above.

The resulting sensor fiber's electronic and optoelectronic properties were then characterized under AC driving conditions. The dependence of the impedance on the driving frequency was measured on one of the detectors inside a 7-cm long fiber section using an LCR Meter, the Hioki LCR HiTESTER 3532-50, Hioki USA, Cranbury, N.J., under a condition of darkness and under a condition of illumination by an LED, using Thorlabs M530L2 LED, Thorlabs, Inc, Newton, N.J. The LED illumination was provided at a distance of about 10 cm from the photoconducting material.

Figure 6A:
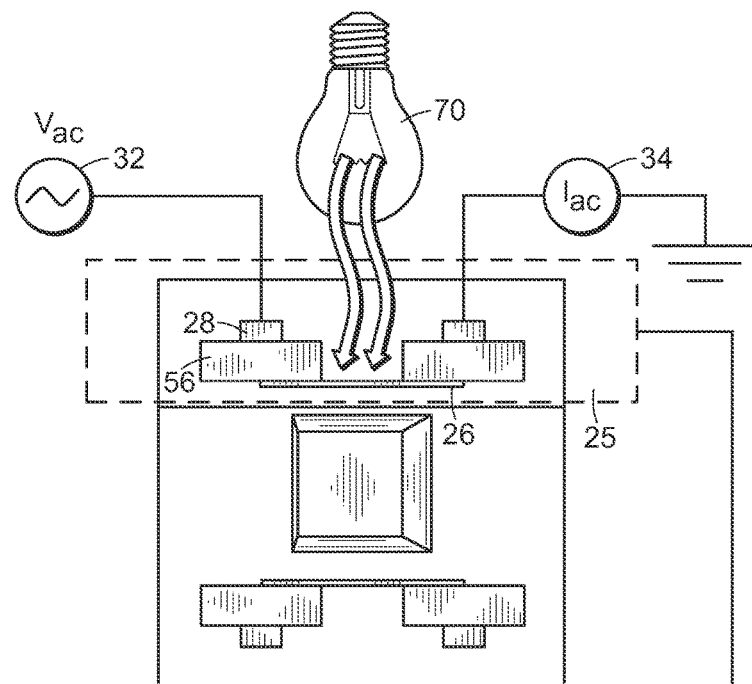
FIG. 6A is a schematic view of a configuration for illuminating a photoconducting material in a sensor fiber for characterizing the sensor fiber photodetector functionality.
Figure 6B:
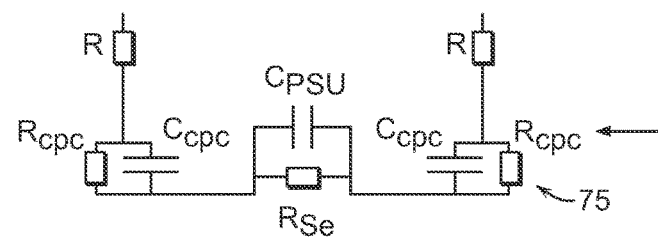
FIG. 6B is a circuit schematic of an equivalent circuit for the sensor fiber configuration of FIG. 6A.

FIG. 6A is a schematic representation of the exterior illumination 70 of the photoconducting material 26 for characterization of one of the sensor fiber's photodetectors 25. FIG. 6B is the equivalent circuit model 75 for the photodetecting structure, and is based on the cross-sectional geometry of the fiber arrangement here. The impedance, Z, of the circuit is given by:

$$Z=2R+2R_{CPC}/(1+jR_{CPC}C_{CPC}\omega)+R_{Se}/(1+jR_{Se}C_{PSU}\omega). \quad (1)$$

where R is the contact resistance and $C_{PSU}$ is the parasitic capacitance between the electrodes; these two parameters are independent from any illumination. $R_{Se}$ is the $Se_{97}S_3$ layer resistance, where the most significant illumination-induced change is expected to occur. $R_{CPC}$ and $C_{CPC}$ are the effective resistance and capacitance of the CPC pads, respectively, which include contributions from the CPC-$Se_{97}S_3$ junction that are affected by illumination as well, though not as significantly as that of the photoconducting material layer.

Figure 6C:
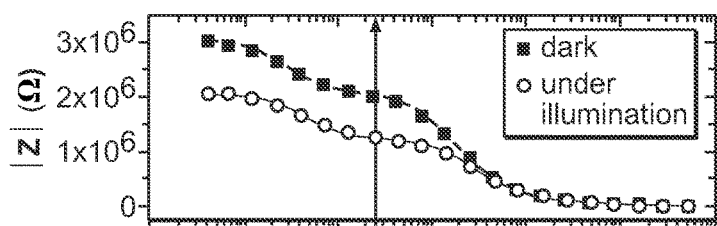
FIGS. 6C-6D are plots of sensor fiber photodetector impedance and ratio of illuminated fiber impedance to dark current fiber impedance, as a function of frequency, respectively.
Figure 6D:
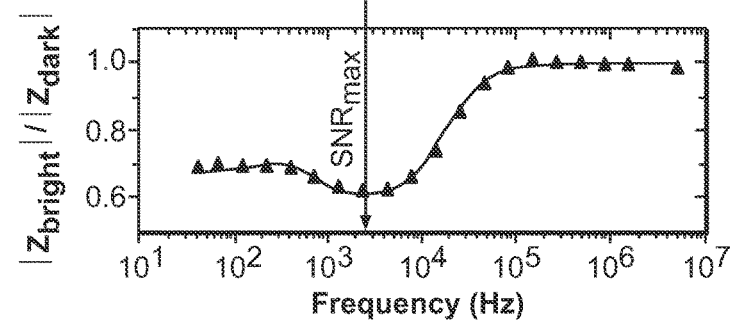

FIG. 6C is a plot of the measured impedance frequency response of the fiber photodetector, given as the absolute value of impedance in the dark, $|Z_{dark}|$, and under illumination, $|Z_{bright}|$. FIG. 6D is a plot of the ratio of the absolute value of the impedance under illumination, $|Z_{bright}|$, to the absolute value of the impedance under dark conditions, $|Z_{dark}|$. Also shown are plotted lines giving the best fits from the equivalent circuit 75 of FIG. 6B. Note that while these measurements were performed with an external illumination source, it is expected that the photo-response of the sensor fiber would be the same for illumination that is generated inside the fiber, because the losses of the PSU cladding are negligible over the distances considered here.

The values of the resistance, R and capacitance of the fiber polymer, $C_{PSU}$, in the equivalent circuit, resulting from the fits to the circuit, were found to be 4 kΩ and 7 pF, respectively. The values of the conductive pad resistance, $R_{CPC}$, the capacitance of the conductive pads, $C_{CPC}$, and the resistance of the photoconducting material, $R_{Se}$, were found to be 498 kΩ, 1162 pF and 2031 kΩ in the dark and 422 kΩ, 950 pF and 1196 kΩ under illumination, respectively, representing a photo-induced change in value of 15%, 18% and 41%, respectively. The very good quality of the fit between the measured data and the equivalent circuit model emphasizes that the simple equivalent circuit suggested here accurately describes the sensor fiber's optoelectronic frequency response. The optical bandwidth of the fiber under a DC driving voltage and sinusoidally modulated optical source was measured to be 400 Hz, which is sufficient for recording chemiluminescent signals resulting from intake of the analyte, having a typical rise time on the order of seconds.

Because the impedance of the fiber photodetector functionality depends on the driving frequency, there was characterized the frequency, $f_{max\ (SNR)}$, at which the signal-to-noise ratio (SNR) performance of the registration setup would be optimal. Note from the plot of FIG. 6D that the ratio of impedances under illumination and in the dark, $|Z_{bright}|/|Z_{dark}|$, is minimized at $f_{min(|Z_{bright}|/|Z_{dark}|)}$=2.3 kHz. At this frequency the photocurrent signal maximally contrasts the dark current background. Because the electrical current noise and the noise equivalent power (NEP) are strongly correlated to the dark current amplitude, the SNR is maximized at this frequency, i.e., $f_{max\ (SNR)}=f_{min(|Z_{bright}|/|Z_{dark}|)}$.

The responsivity, r, of the sensor fiber photodetectors was measured by illuminating the fiber with the aforementioned LED at a known optical intensity and recording the corresponding photocurrent through one of the photodetecting structures. This measurement was performed by driving the fiber and measuring its photo-response with a lock-in amplifier, the Stanford Research System SR810 DSP lock-in amplifier, Stanford Research Systems, Inc., Sunnyvale, Calif., at the optimal driving frequency determined just above, 2.3 kHz, under driving voltage amplitudes ranging from 0V-2 V, for which the responsivity was measured to be invariant when normalized to $I_{dark}$.

Accordingly, the responsivity, r, can be expressed in terms of % of $I_{dark}$ added to the photocurrent per unit of optical flux through the detector area, which was found to be found to be r=0.090±0.003 [% of $I_{dark}$/nW]. This normalized responsivity, r, translates into an actual responsivity of 0.246 nA/nW for a typical dark current of 0.273 µA used in the chemiluminescent measurements described below. Furthermore, noise current measurements for this range of driving voltages revealed that the sensitivity of the signal registration setup was limited at 0.1 nA by the lock-in amplifier resolution rather than by the fiber photodetector itself.

Figure 7A:
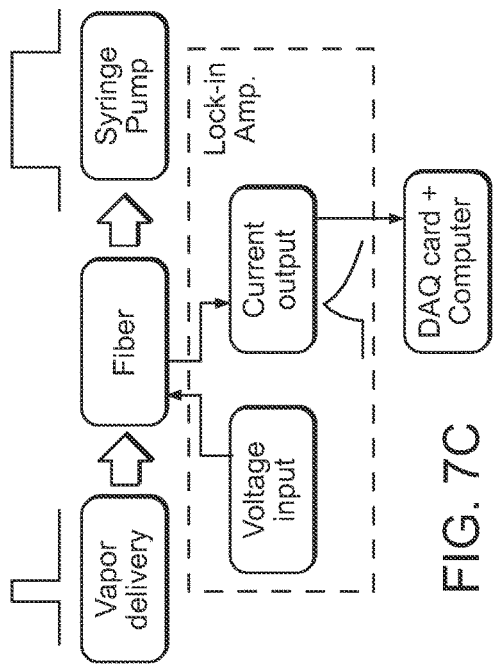
FIGS. 7A-7B are schematic perspective views of an example configuration for arranging a sensor fiber to take in a species to be detected.
Figure 7B:
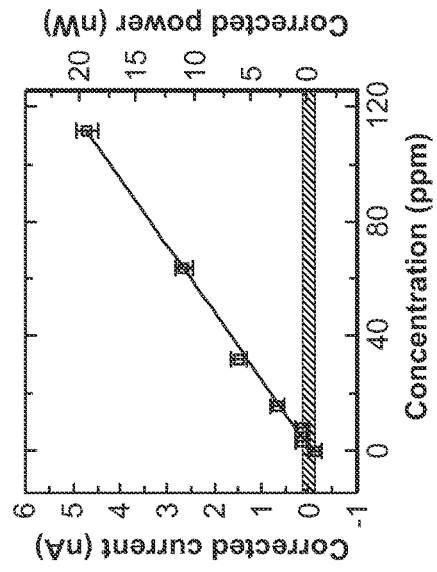
Figure 7C:
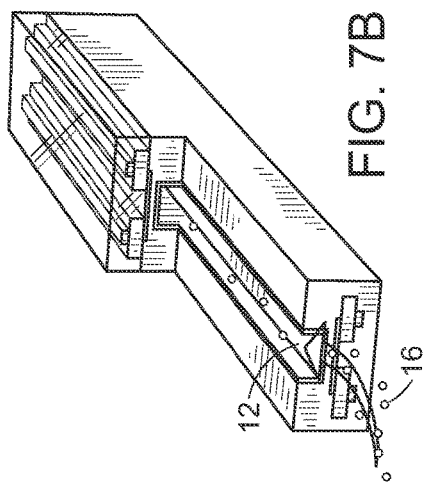
FIG. 7C is a schematic chart of a system configuration for exposing a sensor fiber to a species and for measuring the sensor fiber detection signal.

The sensor fiber was then prepared for sensing a selected species, namely, peroxide, by coating the inner surface of the microcapillary with a transduction element sensing layer. The sensing layer was formed by first producing a mixture of 2 mg oximide powder, 2 mg of phthalate powder, 3 µl of toluene containing 1 mg/ml of fluorescein, and 10 mg/ml of TBAH. The mixture was stirred and heated above 90 deg. C. to become uniformly mixed. One end of the fiber was then dipped into the heated mixture for the mixture to be up taken into the hollow microcapillary of the fiber by the capillary force. The microcapillary was then gently blown out to leave a coating of about 10 µm in thickness on the microcapillary walls. Upon cooling to room temperature, the coating became viscous. One end of the fiber was then hermetically sealed to tubing that was attached to a syringe pump. The opto-fluidic system and electronics setup is shown schematically in FIGS. 7A-B. The sensor fiber was secured into an adaptor 80 that was connected to the flexible tubing of a syringe pump intake. The fiber cladding was removed locally to expose photodetector electrodes 28 and external wires were connected to the individual electrodes. The fiber was inserted into the headspace 84 of a vial 86 containing peroxide solution. With this arrangement, then as shown schematically in FIG. 7B, the peroxide species 16 could enter the fiber hollow conduit 12. FIG. 7C is a block diagram of the set up. A syringe pump delivered peroxide vapor into the fiber. The photodetecting structures in the fiber were electrically driven by a voltage input from a lock-in amplifier and the results of sensing events were registered as an electrical current output signal. The signal was then recorded by a data acquisition card and buffered to a computer.

Figure 7D:
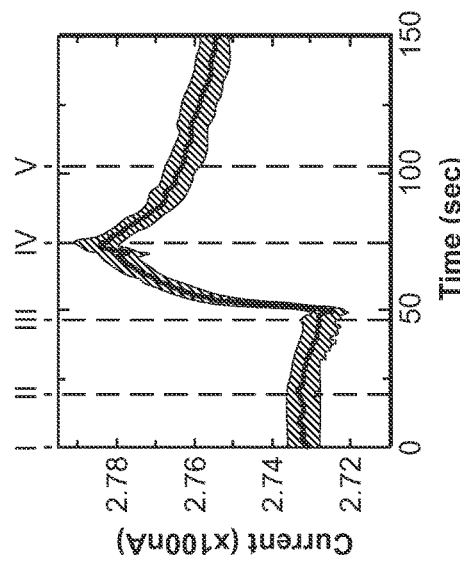
FIGS. 7D-7E are plots of measured detection signal electrical current as a function of fiber exposure time and corrected measured current, as a function of sensed species concentration, respectively.

A standard protocol for measurement was divided into a number of stages. The measurement plot of FIG. 7D provides the measured results, each labeled by a corresponding Roman numeral. First (I), the electrical current in a fiber-embedded photodetector was recorded for 20 seconds in order to obtain a baseline measurement. Second (II), the syringe pump was turned on to a flow rate of 50 cc/min and the fiber was purged for 30 seconds with air. During this phase the current slightly decreased due to the purging of the peroxide residues from the previous measurement. Third (III), the free fiber end was exposed to the headspace of the vial containing an aqueous peroxide solution of known concentration for 20 seconds. Concentrations ranging from 3 ppm to 112 ppm were provided. During this phase vapors of peroxide flowed through the fiber microcapillary and chemically reacted with the sensing layer, causing the layer to luminesce. The resulting light was captured by photodetectors of the fiber, and the lock-in amplifier registered the resulting photocurrent as a current addition to the baseline current. Fourth (IV), the vial was removed while the pump continued to run for an additional 20 seconds. Finally (V), the pump was turned off and the measured electrical current gradually returned to the baseline level.

Figure 7E:
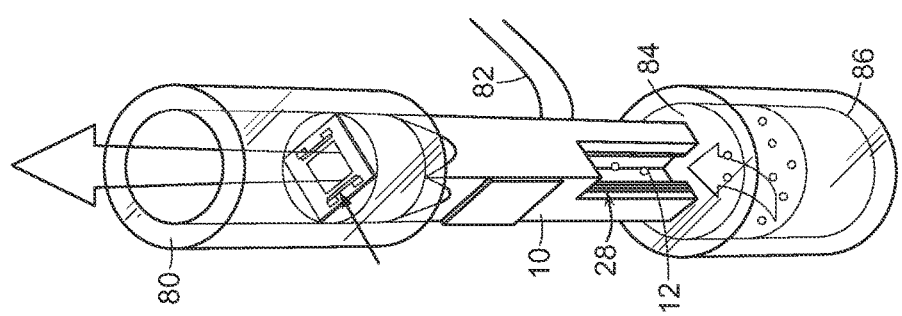

With this protocol, photocurrent measurements were performed for liquid phase peroxide concentrations increasing between 1% and 35%, from which vapor phase concentrations were calculated using Henry's Law. All measurements were performed at the driving frequency of 2.3 kHz while the dark current was 0.273 µA with a driving voltage of 0.5 V. FIG. 7E is a plot of peroxide sensitivity, showing the measured photocurrent produced by the sensor fiber as a function of vapor phase peroxide concentration. These measurements yielded a data line having a slope of 0.043±0.001 nA/ppm and noise current of 0.127 nA (standard deviation over a 1 second interval) as shown in the plot of FIG. 7E. Based on this measured responsivity and dark current, these measurements were translated into a sensitivity curve having a slope of 0.176±0.005 nW/ppm with a noise level of 0.517 nW, corresponding to a NEP of 0.731 nW/√Hz. The detection limit at SNR=1 was found to be 3.0±0.1 ppm for this sensitivity slope and noise level.

To characterize the sensor fiber under optimal conditions, the fiber was integrated into a package that provided heat, at a temperature of ~80° C., to the fiber sensing layer to obtain optimal chemiluminescent efficiency, and that provided a peristaltic pump at a continuous flow rate of 60 cc/min for analyte vapor delivery. The electronics for this setup were limited to operation at a DC voltage. Measurements were performed on a 7-cm section of fiber as above in this example. But for this configuration, the chemiluminescent material was coated on the inner wall of a silica capillary of the same length as the fiber and was then inserted into the fiber's hollow conduit. A 5 V DC bias was applied across the photodetecting structures' electrodes contacted in parallel and the electrical current was registered by an electrometer, the Keithley 6517 electrometer, Keithly Instruments, Cleveland, Ohio.

Figure 8A:
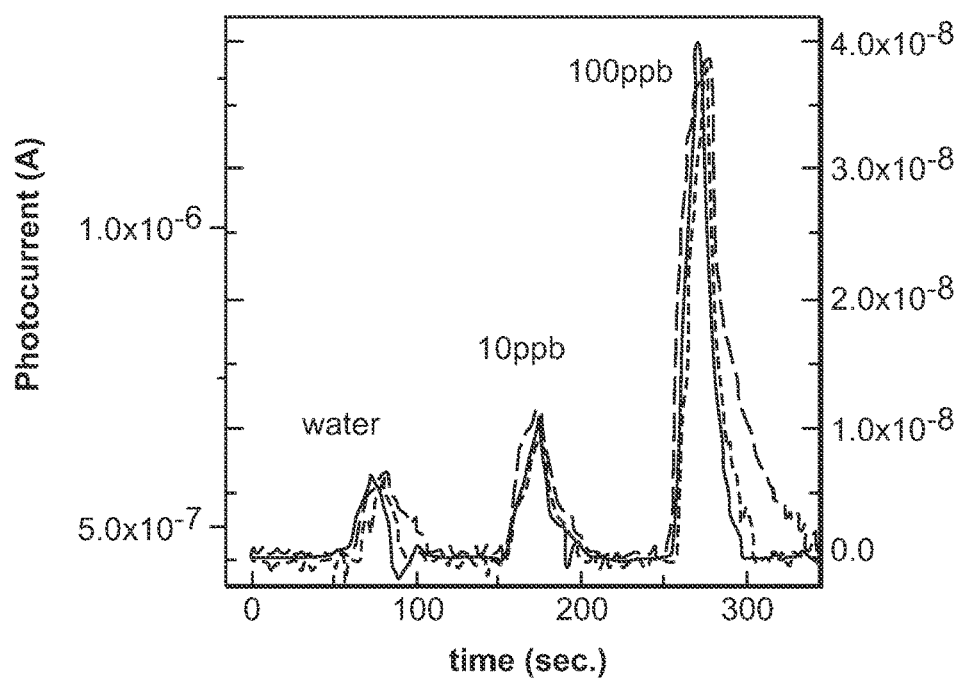
FIGS. 8A-8B are plots of measured signal detection photocurrent produced by an experimental sensor fiber as a function of time.
Figure 8B:
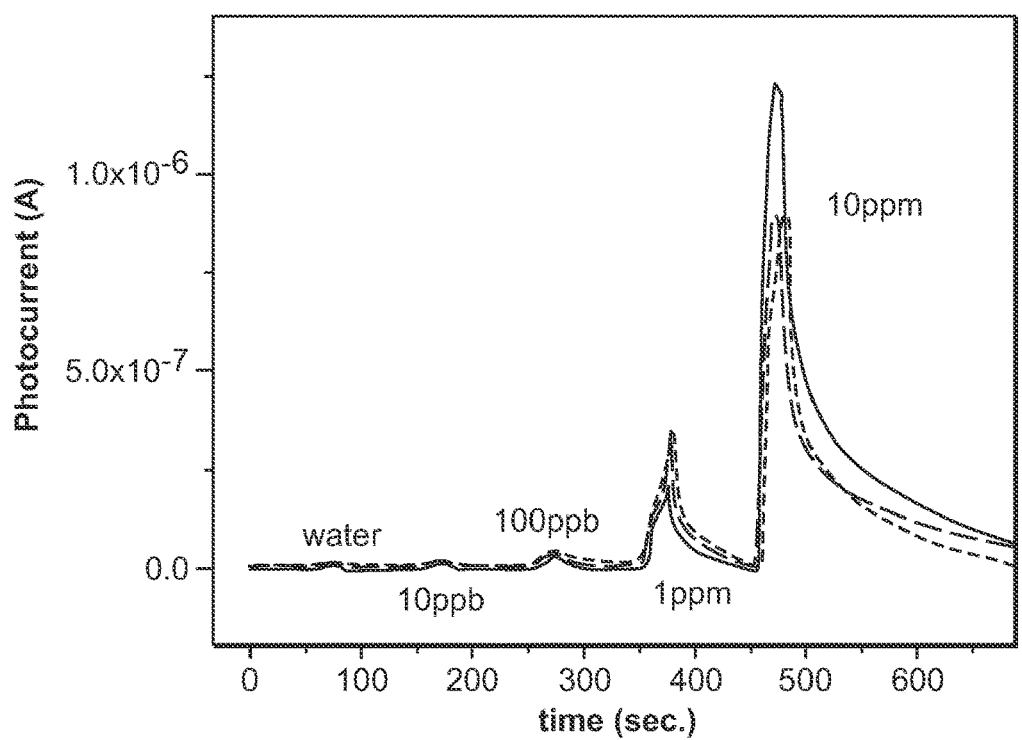

Although heating of the fiber from room temperature up to 80° C. reduced photoconductivity by a factor of three and slightly increased the noise due to a doubling of the dark current, in this configuration the sensor fiber was capable of sensing hydrogen peroxide vapor concentrations as low as 10 ppb, Three sensitivity measurements for this fiber are shown in the plots of FIGS. 8A-8B. This is comparable to state-of-the-art commercially available detectors and is three orders of magnitude more sensitive than the performance depicted in FIG. 7E. About an order of magnitude in this increase is attributed to the higher driving voltage, with the remainder of the increases attributed to the enhancement in chemiluminescent sensing material sensitivity to peroxide at the elevated temperature. Note that in the electrical current measurements, a signal from water sets the detection limit. This signal is not the result of an optical event, but arises from transient heating/cooling of the fiber when moisture-rich air from the headspace of a water-only vial passes through the heated inlet tip of the packaging before entering the fiber. If eliminated by improved fiber temperature stabilization, it is then understood that the limit-of-detection would improve by another order of magnitude and accordingly, it is understood that the sensor fiber would be capable of measuring single ppb level of peroxide vapor.

With this experimental example and the description provided above, it is demonstrated that the sensor fiber provides all-in-fiber functionality for species intake, species interaction with a transduction element, and photodetection, to produce within the fiber an electrical signal indicative of the intake species. The sensor fiber can be adapted for remote as well as distributed sensing, and thereby enables detection and analysis of hazardous or dangerous materials and environments, including explosives. The small footprint, ease of multiplexing, flexible form factor, and compatibility with miniaturized electronics that are characteristic of the sensor fiber enable a wide range of sensing configurations with very high sensitivity.

It is recognized that those skilled in the art may make various modifications and additions to the embodiments described above without departing from the spirit and scope of the present contribution to the art. Accordingly, it is to be understood that the protection sought to be afforded hereby should be deemed to extend to the subject matter claims and all equivalents thereof fairly within the scope of the invention.

We claim:

1. A sensor fiber comprising:
An elongated, unsupported three-dimensional fiber body comprising an electrically insulating polymeric material, the fiber body having a fiber length and an outer fiber body surface along the fiber length, with at least one intake aperture disposed in the fiber body for accepting an intake species into the fiber body;
at least one transduction element comprising a chemiluminescent material disposed within the fiber body along at least a portion of the to fiber length and arranged for exposure to an intake species provided through an intake aperture in the fiber body, the chemiluminescent material emitting chemiluminescent light upon exposure to a target intake species with a wavelength of chemiluminescence indicative of the target intake species;
at least one photoconducting element comprising a semiconducting material arranged in the fiber body in optical communication with the transduction element to receive chemiluminescent light produced by the chemiluminescent material upon reaction of the chemiluminescent material with the target species to produce a corresponding electrical sensing signal indicative of the target intake species; and
at least one pair of electrically conducting electrodes in electrical connection with the photoconducting element in the fiber body, the pair of electrodes extending the fiber length to transmit the electrical sensing signal to an end of the fiber body.

2. The sensor fiber of claim 1 wherein the chemiluminescent material extends the fiber length.

3. The sensor fiber of claim 1 wherein the chemiluminescent material is disposed at an end of the fiber.

4. The sensor fiber of claim 1 wherein the at least one transduction element comprises a plurality of transduction elements, each transduction element in the plurality disposed at a different site along the fiber length.

5. The sensor fiber of claim 1 wherein the chemiluminescent material comprises a layer of chemiluminescent material.

6. The sensor fiber of claim 1 wherein the chemiluminescent material comprises a layer of chemiluminescent material that is disposed on an internal wall of the fiber body.

7. The sensor fiber of claim 1 wherein the at least one transduction element comprises a plurality of transduction elements, each transduction element in the plurality emitting light upon exposure to a different intake species.

8. The sensor fiber of claim 1 wherein the at least one transduction element comprises a plurality of different chemiluminescent materials.

9. The sensor fiber of claim 1 wherein the target intake species comprises one of peroxide vapor and liquid peroxide.

10. The sensor fiber of claim 1 wherein the target intake species comprises 2,4,6-trinitrotoluene.

11. The sensor fiber of claim 1 wherein the target intake species comprises an explosive species.

12. The sensor fiber of claim 1 wherein the at least one transduction element includes a scintillation transduction element that scintillates upon exposure to a radioactive species.

13. The sensor fiber of claim 1 wherein the chemiluminescent material comprises a material selected from the group consisting of fluorescein and naphthofluorescein.

14. A sensor fiber comprising:
an elongated, unsupported three-dimensional fiber body comprising an electrically insulating polymeric material, the fiber body having a fiber length and an outer fiber body surface along the fiber length;
at least one transduction element comprising a chemiluminescent material disposed within the fiber body along at least a portion of the fiber, the chemiluminescent material emitting chemiluminescent light upon exposure to a target intake species with a wavelength of chemiluminescence indicative of the target intake species;
at least one intake microcapillary disposed within the fiber body and extending the fiber length for intake of species to be sensed, the chemiluminescent material being in communication with a microcapillary for exposure of the chemiluminescent material to an intake species;
at least one photoconducting element comprising a semiconducting material arranged in the fiber body in optical communication with the transduction element to receive chemiluminescent light produced by the chemiluminescent material upon reaction of the chemiluminescent material with the target species to produce a corresponding electrical sensing signal indicative of the target intake species; and
at least one pair of electrically conducting electrodes in electrical connection with the photoconducting element in the fiber body, the pair of electrodes extending the fiber length to transmit the electrical sensing signal to an end of the fiber body.

15. The sensor fiber of claim 14 wherein the at least one intake microcapillary comprises a plurality of spaced-apart intake microcapillaries.

16. The sensor fiber of claim 14 wherein the intake microcapillary comprises a hollow fiber core.

17. The sensor fiber of claim 14 wherein the intake microcapillary has a cross section that is generally circular.

18. The sensor fiber of claim 14 wherein the intake microcapillary has a cross section that is generally rectangular.

19. The sensor fiber of claim 1 wherein the electrically insulating material is substantially transparent to a wavelength of light that is generated by the chemiluminescent material.

20. The sensor fiber of claim 1 further comprising at least one microcapillary disposed within the fiber body, extending the fiber length and in fluidic communication with at least one intake aperture and the chemiluminescent material for exposure of the chemiluminescent material to the intake species.

21. The sensor fiber of claim 1 wherein at least one transduction element is disposed in the fiber body at a site adjacent to an intake aperture.

22. The sensor fiber of claim 1 wherein the semiconducting element comprises a chalcogenide glass.

23. The sensor fiber of claim 1 wherein the semiconducting element comprises a chalcogenide glass selected from the group consisting of $Se_{97}S_3$, $As_{24}S_{38}Se_{38}$, and $As_{30}Se_{63}Sb_4Sn_3$.

24. The sensor fiber of claim 1 wherein the photoconducting element comprises a layer of the semiconducting material, extending the fiber length.

25. The sensor fiber of claim 1 wherein the photoconducting element comprises a layer of the semiconducting material, extending the fiber length and including portions of semiconducting material that are crystalline, separated by portions of semiconducting material that are amorphous.

26. The sensor fiber of claim 1 wherein the photoconducting element comprises a semiconducting material having a bandgap energy that is less than about 3 eV.

27. The sensor fiber of claim 1 wherein the photoconducting element comprises a layer of the semiconducting material, disposed in the fiber body, along the fiber length.

28. The sensor fiber of claim 1 wherein the photoconducting element comprises a layer of the semiconducting material disposed in the fiber body adjacent to the transduction element.

29. The sensor fiber of claim 1 wherein the at least one photoconducting element comprises a plurality of different semiconducting materials, each semiconducting material being sensitive to a different wavelength of chemiluminescent light.

30. The sensor fiber of claim 1 wherein the electrodes comprise a material selected from the group of metals and metal alloys.

31. The sensor fiber of claim 1 wherein the electrodes are connected in a photodetector circuit that includes a voltage source connected to apply a bias voltage to the photoconducting element.

32. The sensor fiber of claim 1 wherein the electrodes are connected to deliver an electrical signal from an end of the sensor fiber to an output circuit that includes a current measurement element to measure an indication of photogenerated charge produced by the photoconducting element.

33. The sensor fiber of claim 1 wherein the electrodes are connected to deliver an electrical signal from an end of the sensor fiber to an output circuit that produces an electrical indication of exposure of the transduction element to an intake species.

34. The sensor fiber of claim 1 wherein each electrode is geometrically confined within the fiber body by the electrically insulating material of the fiber body.

* * * * *

UNITED STATES PATENT AND TRADEMARK OFFICE
CERTIFICATE OF CORRECTION

PATENT NO. : 10,338,000 B2
APPLICATION NO. : 14/035933
DATED : July 2, 2019
INVENTOR(S) : Alexander Gumennik et al.

Page 1 of 1

It is certified that error appears in the above-identified patent and that said Letters Patent is hereby corrected as shown below:

On the Title Page

(73) Assignees: Massachusetts Institute of Technology, Cambridge, MA (US);
FLIR Systems, Incorporated, Wilsonville, OR (US)

Should read:
(73) Assignee: Massachusetts Institute of Technology, Cambridge, MA (US)

Signed and Sealed this
Thirty-first Day of March, 2020

Andrei Iancu
*Director of the United States Patent and Trademark Office*